(12) United States Patent
Kakui et al.

(10) Patent No.: US 7,608,404 B2
(45) Date of Patent: Oct. 27, 2009

(54) DISEASE DETERMINATION METHOD, DATA GENERATION METHOD FOR DISEASE DETERMINATION AND DATA GENERATION SYSTEM FOR DISEASE DETERMINATION

(75) Inventors: Akimitsu Kakui, Hamamatsu (JP); Katsu Honzawa, Hamamatsu (JP); Yukiko Sato, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 246 days.

(21) Appl. No.: 10/533,116

(22) PCT Filed: Oct. 30, 2003

(86) PCT No.: PCT/JP03/13935

§ 371 (c)(1),
(2), (4) Date: Jan. 23, 2006

(87) PCT Pub. No.: WO2004/040273

PCT Pub. Date: May 13, 2004

(65) Prior Publication Data

US 2006/0234319 A1 Oct. 19, 2006

(30) Foreign Application Priority Data

Nov. 1, 2002 (JP) ............................. 2002-320044

(51) Int. Cl.
*G01N 33/53* (2006.01)
*G01N 33/566* (2006.01)
(52) U.S. Cl. ...................... 435/7.1; 435/7.92; 436/501; 436/506; 436/518; 424/130.1; 424/178.1; 530/300; 530/350
(58) Field of Classification Search ................ None
See application file for complete search history.

(56) References Cited

U.S. PATENT DOCUMENTS

| 4,559,309 A | 12/1985 | Evenson et al. |
| 5,303,026 A | 4/1994 | Strobl et al. |
| 5,532,166 A | 7/1996 | Ma |

FOREIGN PATENT DOCUMENTS

| CN | 101281131 | * 10/2008 |
| EP | 1 203 944 | 5/2002 |
| JP | 61-100832 | 5/1986 |
| JP | 6-199859 | 7/1994 |
| JP | 09-159609 | 6/1997 |
| JP | 2003-065956 | 3/2003 |
| WO | WO 97/35192 | 9/1997 |
| WO | WO 00/39565 | 7/2000 |
| WO | WO 01/92859 | 12/2001 |
| WO | WO 01/92859 A1 | * 12/2001 |

OTHER PUBLICATIONS

Vince Phelan (American Biotechnology Laboratory, 1995, vol. 13, No. 3, p. 22, ISSN:0749-3223) Abstract Only.*

* cited by examiner

*Primary Examiner*—Lisa V Cook
(74) *Attorney, Agent, or Firm*—Drinker Biddle & Reath LLP

(57) ABSTRACT

Supernatant of the urinary sample (SP1) was mixed with an acid or alkali and heated (SP2) and the sample for fluorescence assay was prepared after adjusting its acidity to alkaline (SP3). Next, using fluorometry, three-dimensional fluorescence spectrum consisted of an excitation light wavelength, fluorescence wavelength and fluorescence intensity (SP4). Then, a relative maximum peak is detected as a specific point in the three-dimensional fluorescence spectrum to specify a specific point attribute (peak number, peak position and fluorescence intensity) and then the urinary sample is sorted based on the attribute (SP5). Finally, the presence or absence of a disease such as a malignant tumor is determined based on the sorting results of the urinary sample (P6).

13 Claims, 16 Drawing Sheets

DISEASE DETERMINATION METHOD, DATA GENERATION METHOD FOR DISEASE DETERMINATION AND DATA GENERATION SYSTEM FOR DISEASE DETERMINATION

TECHNICAL FIELD

The present invention relates to a disease determination method, data generation method for disease determination and data generation system for disease determination, more specifically, the disease determination method, data generation method for disease determination and data generation system for disease determination used to determine specific diseases such as a malignant tumor by examining a urinary sample from the human body.

BACKGROUND ART

As methods to determine whether a person suffers from a certain disease or not or to examine the progress of the disease, methods to examine the body non-invasively or methods to analyze or examine biological samples are widely used. For the latter methods, the method to analyze a chemical substance qualitatively and quantitatively as a biochemical marker, which is uniquely generated in the body when he/she suffers from a certain disease, is generally used.

When such a specific disease is a case of a malignant tumor (cancer), the use of polyamine or pterin in human urine or biological fluids as a biochemical marker is suggested to be clinically significant. In addition, the method using natal pteridine, namely oncopterin as a more reliable marker substance is also suggested (See Japanese Published Unexamined Patent Application No. H6-199859, for example). In the present method, urine collected from the patient was hydrolyzed with acid prior to HPLC analysis and oncopterin in the sample is selectively isolated to measure the amount of oncopterin.

In short, the amount of oncopterin in the sample is obtained by (i) running the sample through an anion exchange column, washing and eluting oncopterin with electrolyte solution, (ii) running the eluant through a cation exchange column, washing and eluting oncopterin with acidic solution and isolating oncopterin with a reverse column, if needed, (i) measuring fluorescence intensity derived from the oncopterin in the eluant, and (iv) calculating the amount of oncopterin based on the intensity using the calibration curve.

Then, when the urinary samples collected from a subject with a suspected malignant tumor and a healthy volunteer (a person who does not have suspected diseases such as a malignant tumor, hereinafter the same) are analyzed in this way and the amount of oncopterin in the urinary sample of the subject is significantly higher than that of the healthy volunteer, it is determined that the subject is likely to have a malignant tumor.

DISCLOSURE OF THE INVENTION

Moreover, it is possible that there are many unknown substances that can be found along with various organic compounds unique to a malignant tumor as described above in the urinary sample of the patients with a malignant tumor. Many of these organic compounds are considered to be autofluorescent components. However, in the above conventional method, the oncopterin in a urinary sample is isolated from the urinary sample to measure the amount of fluorescence emitted therefrom, in other words, only one type of compound is used as a marker for disease determination.

However, when such a method is used, the information of other autofluorescent substances in the urinary sample cannot be obtained. Therefore, veracity and accuracy of disease determination is not sufficient in some cases, which may be inadequate as a clinical diagnostic method. More specifically, sensitivity (ratio that a paerson having a disease is determined as having the disease) or specificity (ratio that a person having no disease is determined as having no disease) may be inconveniently reduced, by contraries, false negative ratio (ratio that a person having a disease is mistakenly determined as not having the certain disease) or false positive ratio (ratio that a person having no disease is mistakenly determined as having a certain disease) may be inconveniently increased. Furthermore, the use of oncopterin as a single marker may become insufficient in terms of its multi-usability and compatibility for the determination of various cancers. In addition, dilution errors which may occur during the pretreatment of a urinary sample and chemical yield errors derived from chemical isolation may decrease the accuracy of the determination.

Furthermore, the labor and time required for the disease determination tends to increase as the amount of fluorescence has to be measured after running the sample for HPLC analysis and processing multiple columns in addition to the pretreatment of the urinary sample. Furthermore, it is likely to be necessary to create a calibration curve for each measurement attempt of fluorescence assay to obtain the absolute value of the oncopterin contained in the sample. Therefore, considering such processes, the labor and time required for the disease determination in total tend to further increase.

Therefore, the present invention has been achieved in view of the above-noted situation and its object is to provide a disease determination method, data generation method for disease determination and data generation system for disease determination to improve the determination accuracy as well as to apply for various disease type determination, furthermore, to facilitate the determination process upon determining whether a person has a certain disease using a sample collected from the body.

To solve the above-mentioned problem, the present inventors extensively studied the biological samples, especially urinary samples from healthy volunteers and patients with malignant tumors to achieve the present invention by discovering that the presence or absence of a malignant tumor in a human body where the urinary sample is collected from can be simply and accurately determined from the urinary sample without qualitative and quantitative analysis of a certain chemical component(s) isolated.

In other words, the disease determination method in accordance with the present invention is a method to determine whether a person has a certain disease or not using a biological sample, comprising, pretreatment process to add acidic or alkaline solution to the sample and to heat the sample, excitation light irradiation process to irradiate the sample with excitation light and to continuously or intermittently change the wavelength of the excitation light, emission light measurement process to measure the wavelength and intensity of the emission light emitted from the sample in response to the excitation light, analyzing and sorting process to detect a specific point in the three-dimensional optical spectrum composed of the excitation light wavelength, emission light wavelength and emission light intensity and to sort or hieiarchize the sample based on the specific point attribute, and determination process to determine the presence or absence of a certain disease or the condition of disease (disease type, degree, progression and urgency) of the person whom the sample belongs to based on the sorting and hierarchization results of the sample.

In addition, the data generation method for disease determination in accordance with the present invention is the data generation method for disease determination using a biological sample obtained from the subject, comprising; pretreatment process to add acidic or alkaline solution to the sample and to heat the sample, excitation light irradiation process to irradiate the sample with the excitation light and to continuously or intermittently change the wavelength of the excitation light, emission light measurement process to measure the wavelength and intensity of the emission light emitted from the sample in response to the excitation light, and analyzing and sorting process to detect a specific point in the three-dimensional optical spectrum composed of the excitation light wavelength, emission light wavelength and emission light intensity and to sort or hierarchize the sample based on the specific point attribute to generate sorting data for disease determination.

The data generation system for disease determination in accordance with the present invention is the data generation system for disease determination to generate disease determination data by analyzing the sample collected from the body of the subject, comprising; excitation light irradiation means to irradiate the sample with the excitation light and to continuously or intermittently change the wavelength of the excitation light, emission light measurement means to measure the wavelength and intensity of the emission light emitted from the sample in response to the excitation light, and analyzing and sorting means to detect a specific point in the three-dimensional optical spectrum composed of the excitation light wavelength, emission light wavelength and emission light intensity and to sort or hierarchize the sample based on the specific point attribute to generate sorting data for disease determination.

In the disease determination method and data generation method for disease determination having the above-mentioned construction, the sample collected from the human body is heated in an acidic or alkaline solution during the pretreatment process to chemically alter, for example, hydrolysis, a part or entire biochemical components in the sample. Then, in the disease determination method, data generation method for disease determination and data generation system for disease determination of the present invention, when the excitation light having various predetermined wavelengths is irradiated to the sample pretreated by the above-mentioned method, autoluminesced molecules in the biochemical component are excited to emit light (mainly as fluorescence) unique to electron transition thereof.

In this way, the wavelength and intensity of the emission light emitted from the sample is measured in the emission light measurement process or by the emission light measurement means as the wavelength and intensity change depending on the type and amount of the autoluminescent component in the sample as well as the wavelength and intensity of the excitation light. In other words, spectrometry is carried out to measure the wavelength and intensity of the emission light in response to the wavelength of irradiated excitation light to obtain the three-dimensional optical spectrum.

Next, in the analyzing and sorting process and the analyzing and sorting means, based on the results of the three-dimensional optical spectrum obtained, a specific point in the three-dimensional coordinate system consisting of excitation light wavelength, emission light wavelength and emission light intensity, for example, an area of the emission light intensity relatively larger than the periphery (more specifically, peak position and relative maximum value position can be illustrated) is detected, and for example, the specific point is specified by its wavelength coordinate. Then, in the analyzing and sorting process and the analyzing and sorting means, the corresponding sample is sorted or hierarchized to a certain group based on the information of the specific point attribute (each specific point if there are more than one specific point that exits).

Here, the specific point attribute includes, for example, wavelength coordinate of the specific point, number of specific points, intensity of emission light on the specific point, rate of change of the emission light intensity near the specific point, overall shape of the three-dimensional optical spectrum (approximate function, changes in primary and secondary derivatives, half-value width or one-tenth value width of maximum peak and peak symmetry, etc.) and it is preferable to determine the specific point attribute by at least one of these parameters in the analyzing and sorting process and the analyzing and sorting means. In addition, the number of "specific point" as attribute is a concept covering when the specific point is 0 and when the specific point is more than 1, namely a parameter including the "presence or absence of the specific point."

The inventors of the present invention determined the attribute by applying these parameters for the specific point that appeared in various three-dimensional optical spectrum obtained from a number of urinary samples (the samples whether the presence or absence of a disease is known). Then, when the urinary samples showing the specific point having similar attributes are grouped into the same sample group, it was determined that the samples collected from healthy volunteers can be extremely sensitively discriminated (differentiated) from the sample collected from the patients. In short, based on the specific point attributes of the subject sample, the subject sample can be sorted by either the sample related to the body likely to be a healthy volunteer or the sample related to the body likely to have disease. In addition, the parameters used to determine these attributes are parameters independent from each other, therefore systematic hierarchical classification of the samples can be achieved by using these parameters in an appropriate order to discriminate the specific point.

Then, in the determination process, whether a person whom the sample belongs to has a certain disease or not and the condition of the disease if he/she has the disease will be determined based on the sorting or hierarchical results. In short, in accordance with the disease determination method and data generation method for disease determination of the present invention, since the sorting or hierarchized results of the sample are obtained as the disease determination data to be used for disease determination without chemically isolating a specific sample in the urinary sample nor qualitative analyzing or quantitative analyzing the sample from the wavelength and intensity of the emission light, sample determination for the specific disease such as a malignant tumor and such will be carried out based on these data In addition, in accordance with the data generation system for disease determination of the present invention, the sorting or hierarchized results for disease determination to be used for disease determination described above can be preferably obtained.

Now, for the samples used for the present invention, all biological samples collected for regular in vitro diagnosis such as serum, plasma, urine, cerebrospinal fluid, amniotic fluid, ascitic fluid and lymph fluid as well as washings or extract of tissue and cell solvent can be included. Among them, urine and serum samples are preferably used. Among them, the use of urinary samples are most preferred since the urinary sample is more suitable for the use of the present invention in terms that the sample can be collected without causing the subject pain unlike collecting a blood sample, and that the urinary sample is more easy to generate three-dimensional spectrometry profile by measuring the emission light.

In addition, it is preferable to perform data correction, namely to standardize the intensity of emission light with the emission light intensity on certain excitation light wavelength and emission light wavelength- With this procedure, when a plurality of samples exist and the intensities of their emission light have to be compared among these samples, the difference in the sample concentration in the fluorescence assay sample derived from individual physiological phenomenon can be balanced out. In addition, such correction is not limited to the method described above and, for example, a method to standardize with the concentration of the known substances found in the same urinary sample, such as creatinine can be used.

In addition, as described above, the emission light from the sample is considered to be mainly derived from the autoluminescent components, therefore, it is preferable to measure fluorescence as the emission light. Furthermore, in the excitation light irradiation process and the excitation light irradiation means, it is useful to preferably use a light having a wavelength in a range of 200-900 nm, or more preferably 300-600 nm as an excitation light and in the emission light measurement process and the emission light measurement means, it is useful to preferably measure a light having a wavelength in a range of 200-900 nm, or more preferably 350-600 nm as the emission light.

In addition, it is preferable to add an acidity adjustment process to adjust the acidity of the sample after the pretreatment process is performed and in the acidity adjustment process, it is more preferable to arbitrarily select the acidity of the sample solution from acidic or alkaline, neutral or almost neutral solution to adjust its acidity as selected by adding acid, alkali or a buffer.

According to the findings achieved by the inventors of the present invention, autoluminescent light was dramatically observed when the acidity of the urinary sample solution in which no significant autoluminescent was observed when the excitation light was irradiated only after the pretreatment process, was adjusted to alkaline solution (alkaline in the pH range or high alkaline higher than the pH range). In addition, there are some urinary samples among these samples, which show changes in the wavelength and intensity of the autoluminescent emission light when the acidity of the sample solution is changed to acidic, alkaline or neutral solution. With these findings, the usefulness of the acidity adjustment to the urinary sample after the pretreatment process and the appropriate selection of the acidity was proved. For example, it may be useful to change the acidity of the sample solution to alkaline, neutral, almost neutral or acidic solution to complexly and complementarily combine the results obtained from their three-dimensional spectrometry when the disease differentiation was difficult when only the pretreatment process was performed on the sample.

Furthermore, it is considered that there are a number of autoluminescent components unique to a certain disease in the urinary sample and such components having common molecular structure emit light with similar luminescent wavelengths to each other. In this case, in the three-dimensional optical spectrum, luminescent peak of a specific wavelength from such an autoluminescent component or such group can be observed. Therefore, it is preferable to select the relative maximum peak of the emission light intensity in the three-dimensional optical spectrum as a specific point in the analyzing and sorting process or the analyzing and sorting means. In addition, it is also preferable to select the relative minimum peak of the emission light intensity or a point having a $1/n$ of the intensity of the relative maximum peak value (n>1) in the three dimensional optical spectrum as a specific point.

However, there is a case that there is no sharp luminescent peak recognized in the three-dimensional optical spectrum due to the peak shift caused by the differences in functional groups of the autoluminescent components, relaxation during the luminescent process or inelastic scattering in the autoluminescent samples. Therefore, as described above, it is preferable to specify the wavelength coordinate of the excitation light and emission light which the intensity of the emission light in the three-dimensional coordinate system was significantly higher from the periphery in the analyzing and sorting process or the analyzing and sorting means. In this way, the specific point can be easily detected and specified when the application of function fitting, which is frequently used for peak analysis used in general spectrometry, is difficult, for example, when the intensity disruption of the emission light is so broad or so asymmetric that function approximation cannot be performed.

More specifically, in the analyzing and sorting process, it is preferable to create maps for specific point detection, consisting of a numerical matrix, contour map or vector diagram in the three-dimensional coordinate system to specify the specific point based on these specific point detection maps.

Now, as an example of "numerical matrix," excitation light wavelength is plotted on one factor of the two-dimensional matrix (row, for example) and an emission light wavelength is plotted on the other factor (column, for example) and a matrix having the value of the emission light intensity as matrix components can be used. Using this, for example, the presence of a specific point is specified on the position (wavelength coordinate) larger than a plurality of matrix components (8, for example) in the vicinity on a 3×3 matrix.

In addition, as an example of a "contour map," an excitation light wavelength is plotted on one axis of the two-dimensional coordinate and an emission light wavelength is plotted on the other axis, and then the figures made of horizontal lines are created by connecting the coordinates having the same emission light intensity. Using this, for example, the presence of a specific point is specified on the inner center of a plurality of closed cues or a position in the vicinity (wavelength coordinate).

Furthermore, "vector diagram" is a matrix for which its matrix component is depicted with lines of vectors having the direction increasing the emission light wavelength when excitation light wavelength is plotted on one factor (row, for example) of the two-dimensional matrix and emission light wavelength is plotted on the other factor (column, for example). Using this, for example, the presence of a specific point is specified on the position where the direction of vector lines of each matrix factor cross or converge (wavelength coordinate).

In addition, in the analyzing and sorting process or the analyzing and sorting means, it is also preferable to sort the samples based on the results of comparison between the known specific point attribute of the detected in advance using the already known standard sample from the body having a certain disease with the specific point attribute obtained from the sample used for determination.

In this way, more detailed sample sorting is promptly performed by directly comparing the specific point attribute detected in the sample collected from the subject with the known specific point attribute prepared in advance, which was obtained from the samples from different disease sites of the specific disease in the three-dimensional optical spectrum.

Especially, it is preferable to have a standard data generation process or standard data generation means to generate the known specific point attribute in advance to be used for the criterion of differentiating the sample from the patient having this disease from the sample from a healthy volunteer based on the comparison between the three-dimensional optical spectrum of the sample collected from the healthy body and the three-dimensional optical spectrum of the sample collected from the patient having the known disease.

According to this method, the specific point attribute uniquely found only in the biological sample having a specific disease or the combination of the specific point attribute as standard data for sample sorting can be easily generated. Therefore, sorting is easily performed by matching the sample from the subject with the biological sample from the healthy body or from the body with a specific disease through the comparison of the specific point attribute obtained from the sample of the subject tested for determination with the known specific point attribute collected as described above. In addition, according to this comparison, a plurality of specific point attributes suitable for discrimination for one type of disease can be obtained and then, these attributes can be combined to compare the sample from the subject to further facilitate hierarchical sorting of the subject sample. Therefore, sorting or hierarchized results enabling highly sensitive disease determination of the subject samples is generated.

In addition, the present invention is especially useful when a certain disease is a case of a malignant tumor. In this case, it is desirable to maintain the sample solution to be alkaline during the acidity adjustment process.

BEST MODES FOR CARRYING OUT THE INVENTION

The embodiment of the present invention will be described in detail hereinafter.

FIRST EMBODIMENT

Figure 1:
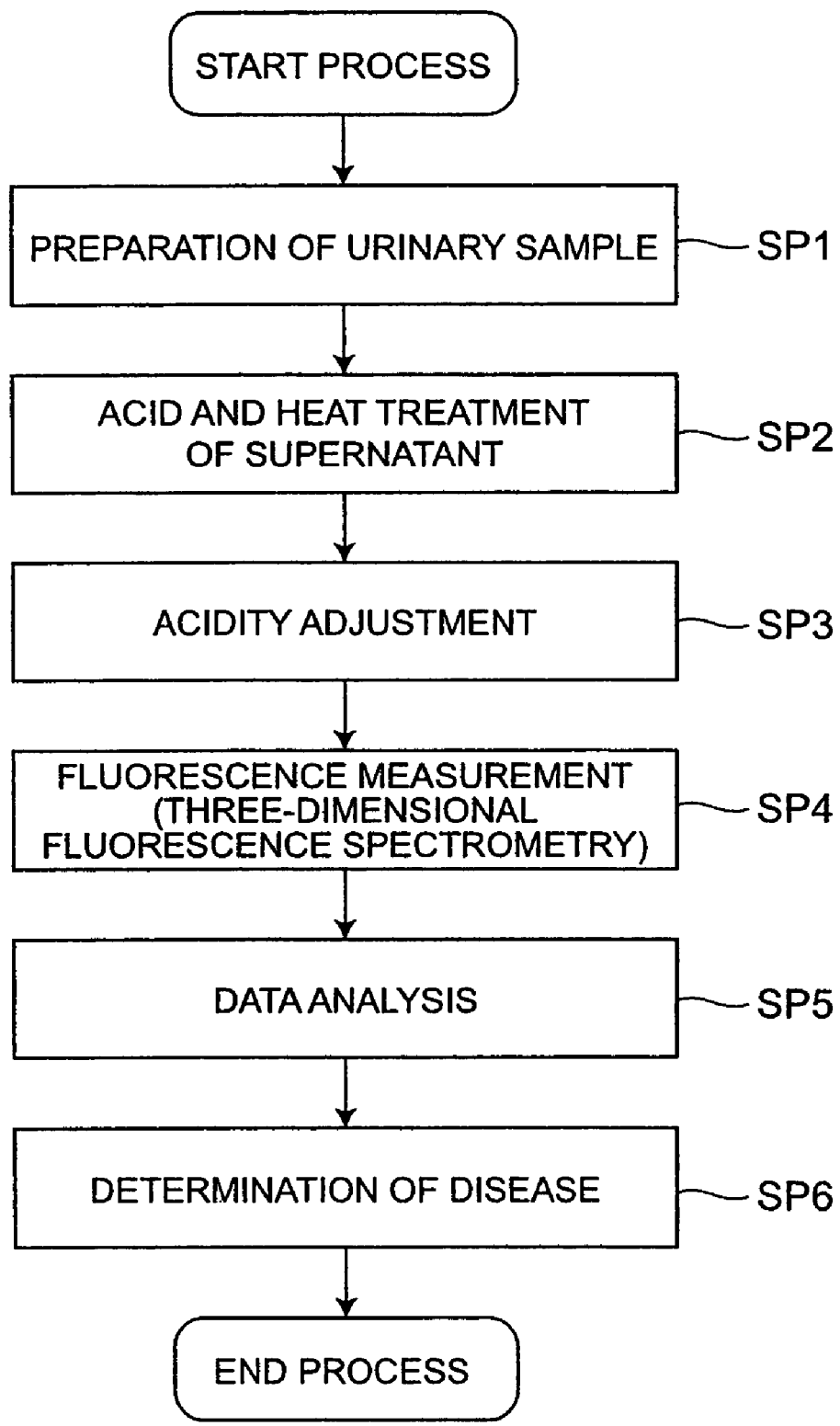
FIG. 1 is a flowchart to perform the preferable first embodiment, such as the method for disease determination, of the present invention.

FIG. 1 is a flowchart showing a procedure to perform the preferable first embodiment of the disease determination method and data generation method for disease determination of the present invention.

(Pretreatment of the Urinary Sample)

First, urine is collected from a subject to prepare a urine sample (step SP1). Next, the urinary sample is centrifuged to separate the liquid component from fine solid components and the supernatant is collected. Then, the supernatant is transferred to a sealed pressure vessel such as a test tube with a screw cap, then the supernatant is mixed after the addition of acid such as hydrochloric acid, and incubated for a certain period of time while heating at a certain temperature to perform adding acid and heating process of a urinary sample supernatant (step SP2; pretreatment process). With this step, a part or an entire part of the biochemical component in the supernatant is subject to make chemical reactions such as hydrolysis.

Here, the amount of 0.1-10 parts by mass, more preferably 0.2-5 parts by mass of 6 mol/L liter, the same hereinafter) hydrochloric acid can be used as acid for 1 part by mass of the supernatant. In addition, it is preferable to heat at the heating temperature of 100-200° C., more preferably 100-160° C. with a heating time of 0.5-5 hours, more preferably 0.7-2 hours during the pretreatment process.

(Acidity Adjustment of the Urinary Sample)

Next, after the pretreatment process is completed, the supernatant is cooled down to room temperature, is diluted appropriately with a fixed amount of sodium hydroxide solution to adjust its acidity to alkaline to prepare the sample for fluorescence assay (step SP3; acidity adjustment process). At this time, the alkali concentration is not to be limited to a specific range, but can be in a range of pH domain (alkaline). However, in terms of easiness to adjust, it is preferable to adjust the concentration of the OH ion to be 0.01-2 mol/L, more preferably 0.1-2 mol/L when sodium hydroxide is used, for example.

(Fluorescence Measurement of the Urinary Sample)

Next, a fixed amount of the fluorescent sample is added to a fluorescence measurement container, such as a quartz cell to place the container in a regular fluorometer. Then, an excitation light having a predetermined wavelength is irradiated (excitation light irradiation process) to a sample for fluorescence assay and then, a predetermined wavelength of the fluorescence intensity emitted from the sample is measured (emission light measurement process). With this procedure, the three-dimensional fluorescence spectrum (three-dimensional optical spectrum) of an excitation light wavelength, fluorescence wavelength, and fluorescence intensity (step SP4) is created. In addition, it is desirable to maintain the sample at a certain temperature such as room temperature, for example, upon measuring fluorescence.

At this time, it is preferable to continuously scan the wavelength of light having 200-900 nm, more preferably 300-600 nm as an excitation light for irridation. This is because the range of the above wavelength is suitable for one-photon excitation of the autoluminescent component in the urinary sample. In addition, it is possible to use a longer wavelength of light for two-photon excitation to deliver less damage to the sample. At this time, it is preferable to continuously scan the wavelength of light having 400-1800 nm, more preferably 600-1200 nm as an excitation light for irradiation.

In contrast, it is preferable to measure the fluorescence wavelength at the range of 200-900 nm, more preferably 350-600 nm. This wavelength corresponds to one-photon excitation by the excitation light in the above suitable range and at the same time, the fluorescence wavelength from the autoluminescent component in the urinary sample is fully covered in this manner.

(Data Analysis)

Figure 2:
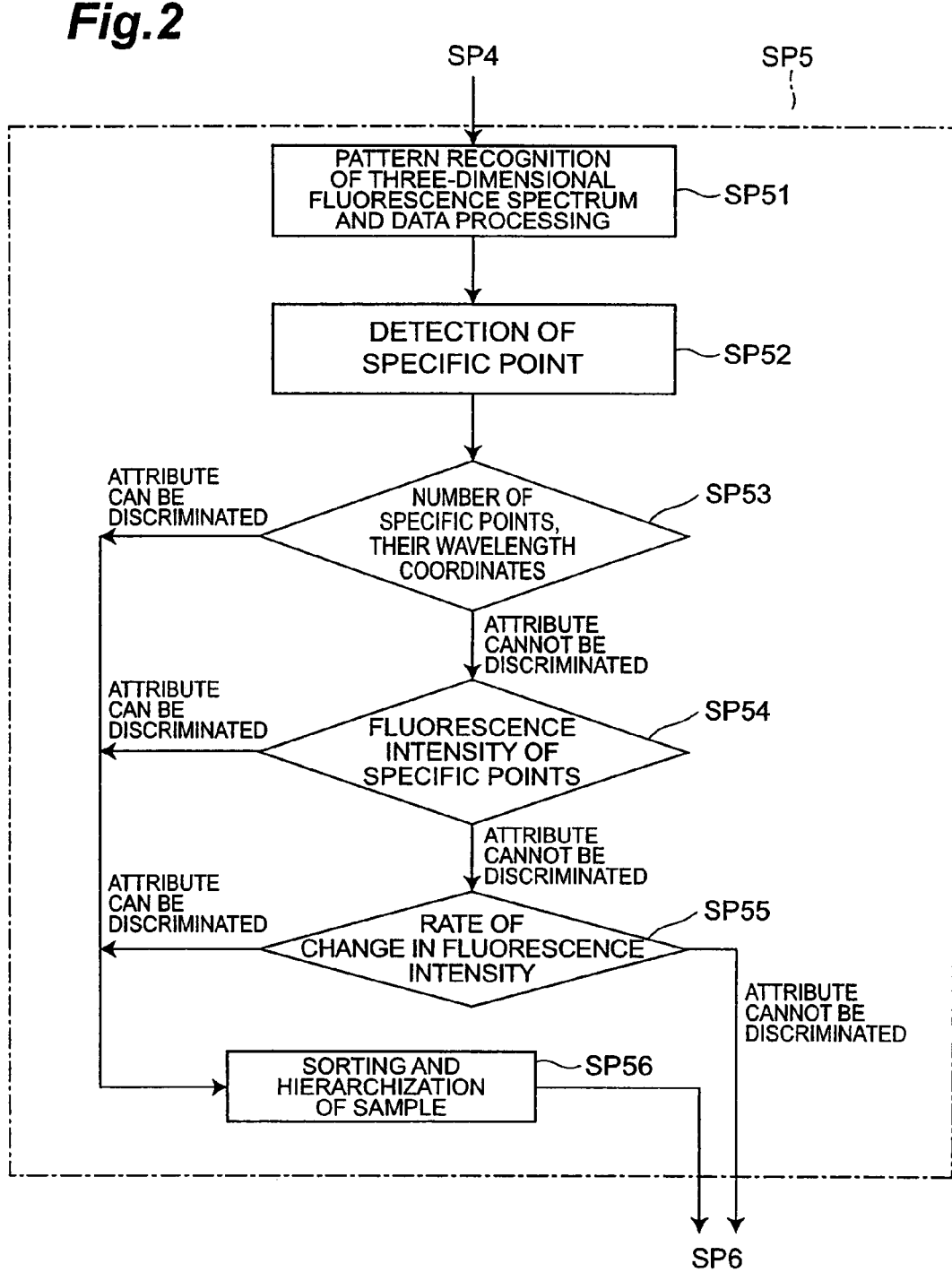
FIG. 2 is a flowchart showing a procedure (scheme) of a preferable embodiment in step SP5 of FIG. 1.

Next, the data analysis will be carried out using the three-dimensional fluorescence spectrum obtained (step SP5; analyzing and sorting process). FIG. 2 shows a flowchart showing the procedure (scheme) of a preferable embodiment mainly in step SP5. In step SP5, first, shape recognition software of a well-known pattern recognition method, is used for recognition (step SP51). More specifically, in the three-dimensional fluorescence spectrum, whether there is an area where its fluorescence intensity is relatively higher than that of periphery, namely the presence or absence of the specific point is preliminarily determined.

Next, in step SP51, the three-dimensional spectrum data will be further processed. This process is for the detection of specific point performed after step SP52. In short, the specific point detection map consists of (1) numerical matrix, (2) contour map, and (3) vector diagram in the three-dimensional coordinate system (system consisting of excitation light wavelength, fluorescence wavelength, and fluorescence intensity) of the three-dimensional spectrum Now, FIG. 3 shows a schematic diagram of a numerical matrix, an example of the specific point detection map, FIG. 4 shows a schematic diagram of a contour map, an example of the specific point detection map, and FIG. 5 shows a schematic diagram of a vector diagram, an example of the specific point detection map.

Figure 3:
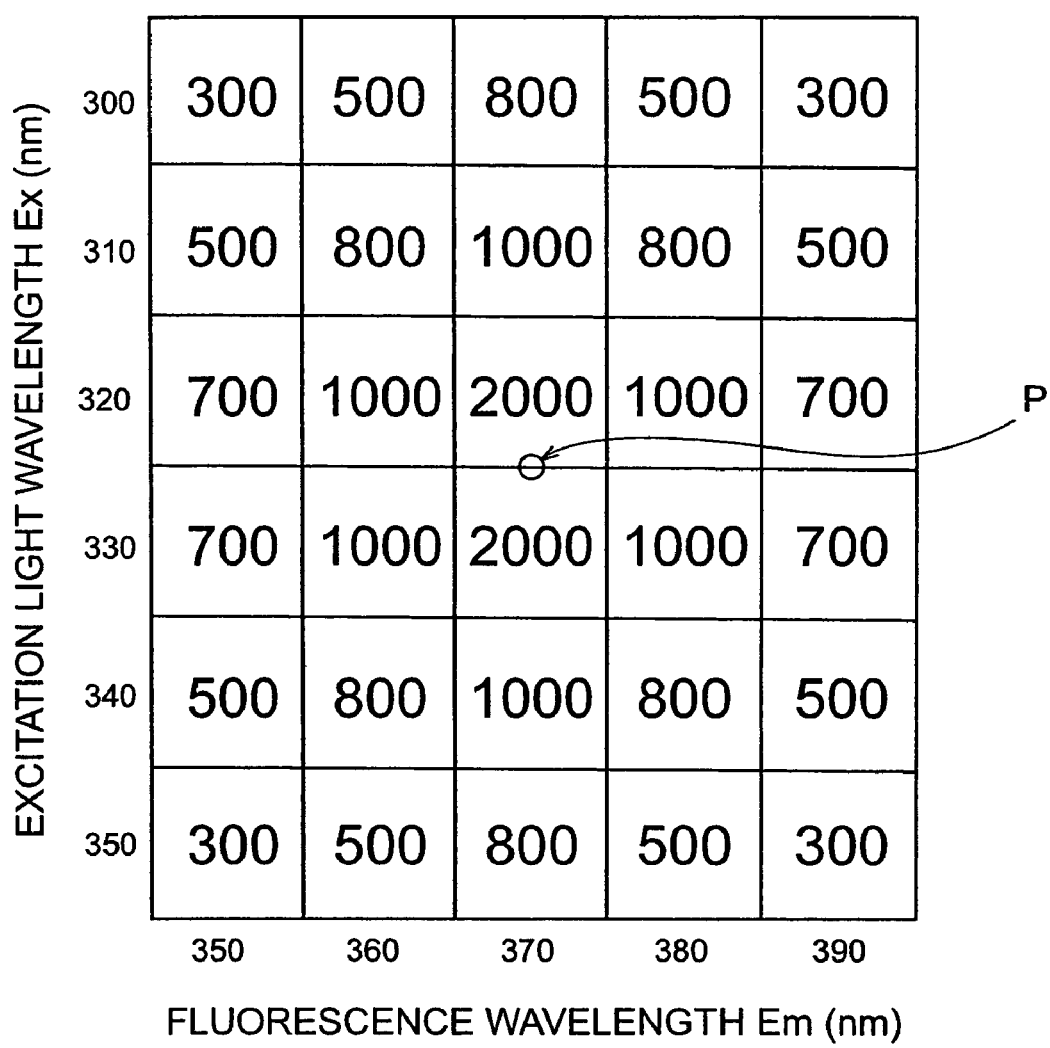
FIG. 3 shows a schematic diagram of a numerical matrix as an example of the specific point detection map.

The specific point detection map shown in FIG. 3 is a 6×5 two-dimensional matrix mapped with the integrated, average or representative values of the measured fluorescence intensity of corresponding wavelength coordinate where row factor and column factor are represented by excitation light wavelength Ex(nm) (10 nm for each grid) and fluorescence wavelength Em(nm), respectively. In this example, there is a relative maximum value having a larger value than a plurality of periphery matrix components and its wavelength coordinate, which is shown by P in the figure, is 320-330 nm (325 nm when it is shown with a median value) for the excitation light wavelength Ex and 370 nm for the fluorescence wavelength (the wavelength coordinate will be expressed such as "Ex/Em=325 nm/370 nm" hereinafter). Then, the relative maximum peak P is specified as a specific point (step SP52).

Figure 4:
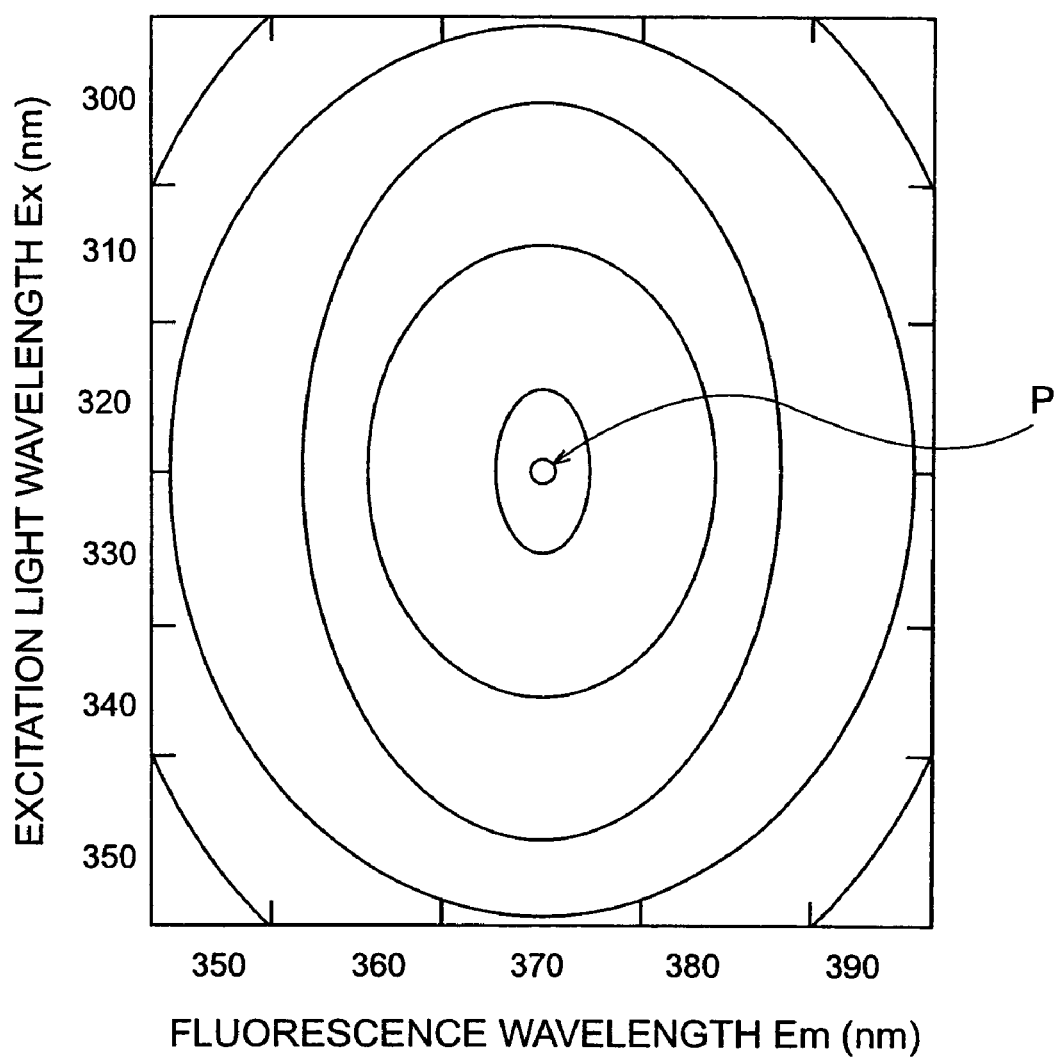
FIG. 4 shows a schematic diagram of a contour map as an example of the specific point detection map.

The specific point detection map shown in FIG. 4 is the figure made of horizontal lines, representing contour lines, created by connecting the coordinates having the same fluorescence intensity with a solid line in a planar coordinate system where the excitation light wavelength Ex is plotted on a Y axis, whereas the fluorescence wavelength Em is plotted on an X axis. For ease of explanation, here, the contour map which was created based on the numerical data of the matrix shown in FIG. 3 will be used. In this example, the relative maximum peak P exists in an inner center of a plurality of closed curves or in the vicinity, namely the relative maximum peak P exists at Ex/Em=325 nm/370 nm and it is specified as a specific point (step SP52).

Figure 5:
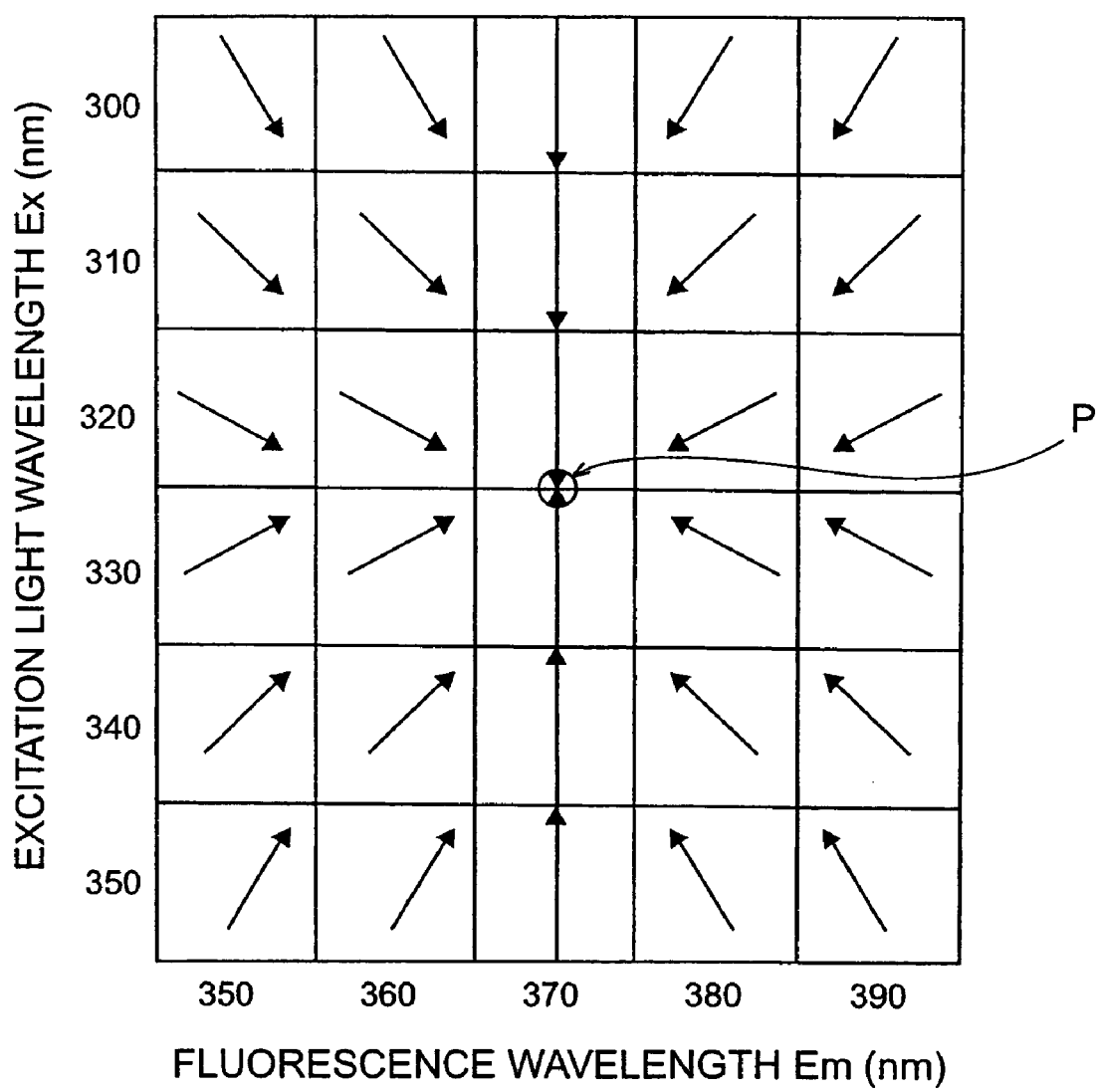
FIG. 5 shows a schematic diagram of a vector diagram as an example of the specific point detection map.

The specific point detection map shown in FIG. 5 is a vector diagram of a 6×5 two-dimensional matrix plotted with vector lines shown with linear arrows in the figure using the matrix composed similarly to the map shown in FIG. 3. For ease of explanation, here, an example of the vector diagram which was created based on the numerical data of the matrix shown in FIG. 3 will be used. Each vector line two-dimensionally represents increasing and decreasing directions of fluorescence intensities in the shapes of the three-dimensional spectrum and represents the direction of incline of the contour map shown in FIG. 4. In this example, there is the point where the extensions of directions of each vector line are crossed, namely the relative maximum peak P exists at Ex/Em=325 nm/370 nm and it is specified as a specific point (step SP52).

Next, the specific point attribute is determined and the specific point is discriminate or grouped based on its attribute. The specific point attribute includes a wavelength coordinate of the specific point (excitation light wavelength Ex/fluorescence wavelength Em), number of the specific points, fluorescence intensity on the specific point, rate of change of the fluorescence intensity near the specific point and overall shape of the three-dimensional fluorescence spectrum (approximate function form, changes in primary and secondary derivative values, half-value width or one-tenth value width of relative maximum peak and peak symmetry). Taking a case of the relative maximum peak P as a specific point specified in the specific point detection map shown in the above-mentioned FIG. 3 to FIG. 5, its attribute is expressed as wavelength coordinate Ex/Em=325 nm/370 nm, peak number=1, fluorescence intensity=approximately 2000, rate of change of the fluorescence intensity near the specific point=an interval of the contour lines of the contour map shown in FIG. 4.

Based on the specific point attribute determined in his manner, the specific point specified for the urinary sample from a subject is discriminated from a specific point pre-specified for the urinary samples from healthy volunteers based on the number of specific points and their wavelength coordinates in step SP53 shown in FIG. 2. More specifically, when the number of maximum peaks and/or peak positions (wavelength coordinates) recognized from the urinary sample from the subject, is/are different from those of the healthy volunteers, discrimination of attributes is possible and the process is shifted to step SP56 described later. When it is not, the discrimination by the number of specific points and their wavelength coordinates is not possible, and the process shifts to step SP54.

Next, in step SP54, the two specific points are discriminated by the fluorescence intensities at these specific points. More specifically, even when the number of maximum peaks and peak position are the same, if the fluorescence intensities at their maximum peaks are significantly different, the discrimination is possible and the process shifts to step SP56. When it is not, the discrimination by the number of specific points, their wavelength coordinates and their fluorescence intensities is not possible, the process shifts to step SP55.

Next, in step SP55, the two specific points are discriminated by the rate of change of the fluorescence intensity near the specific point or overall shape of the three-dimensional fluorescence spectrum. More specifically, even when the number of maximum peaks, peak position and fluorescence intensities of the peak position are the same, if there are significant differences in the contour line intervals and patterns shown in FIG. 4, discrimination is possible and the process shifts to step SP56. When it is not, the discrimination by the number of specific points, their wavelength coordinates, their fluorescence intensities and the rate of change of the fluorescence intensity, etc., is not possible, the process is terminated and the processes after step SP4 are carried out again after adjusting the acidity of the supernatant of the urinary sample where step SP2 shown in FIG. 1 was carried out, to be acidic, neutral or almost neutral with an acid or buffer, instead of the earlier step in which the acidity was adjusted to be alkaline in step SP3. Alternatively, the process shifts to step SP6 by skipping step SP56 to be described later. In addition, only the latter case was described in FIG. 2.

The urinary samples in which the specific point attribute was discriminated in this manner, are grouped (sorted) or categorized (hierarchized) according to the stepwise discrimination scheme as in steps SP53 to SP55. The results of such grouping and categorization correspond to the disease determination data. In addition, steps SP1 to SP5 correspond to the data generation method for disease determination. In addition, the process of shifting from step SP55 to Step 6 by skipping step SP56 indicates that the sample of the subject is sorted to be identical to that of a healthy volunteer.

Then, according to the group and category that each urinary sample belongs to, whether a subject (body) where the urinary sample was collected from has a disease such as malignant tumor or not or how the disease condition is when he/she has the disease, are determined (step SP6; determination process).

In accordance to the disease determination method and data generation method for disease determination of the present invention, instead of analysing qualitatively and quantitatively only a specific biochemical maker found in a urinary sample, the urinary sample, in which only the pretreatment is completed but not chemically isolated, is irradiated with excitation light to non-selectively measure fluorescence components emitted therefrom and the data are analyzed based on these results, so that the information obtained from the urinary sample are dramatically increased. Therefore, the sensitivity, veracity and accuracy of the disease determination are increased.

In addition, the disease determination method in accordance with the present invention is quite useful as a primary screening for disease detection, especially for early detection of a malignant tumor since the sensitivity, veracity and accuracy for disease determination is improved in this manner. Therefore, a variety of primary and metastatic malignant tumors are diagnosed using the disease determination method of the present invention and includes the following tumor types represented as examples: breast cancer, prostate cancer, liver cancer, lung cancer, colorectal cancer, stomach cancer, pancreatic cancer, bladder cancer, head and neck cancer, kidney cancer, cervical cancer, uterine cancer, thyroid cancer, brain tumor, tongue cancer, lymphoma, multiple myeloma, melanoma and leukemia, etc. In accordance with the disease determination method of the present invention, these malignant tumors can be determined at various stages, especially at the first stage, for example, a malignant tumor is fully recognized against the presence of a benign tumor or absence of a malignant tumor of a screened subject.

Furthermore, in the conventional disease determination method using urine analysis, the disease is detected from the absolute value of a biochemical marker found in urine, dilution errors and chemical yield errors which may occur during the pretreatment of a urinary sample may decrease the accuracy of the determination, whereas, the present invention does not rely on the absolute value of a biochemical marker in urine since the number of maximum peaks, its fluorescence intensities and the shapes of three-dimensional spectrum are relatively compared. Therefore, the errors in dilution and chemical yields are eliminated to further increase the determination accuracy.

In addition, this method sufficiently reduces the rates of false negative and false positive to reduce misdiagnosis. Therefore, burden to the subjects and detailed examination burden will be reduced when extensive examination is performed by combining with other clinical examinations. In addition, disease determination not limited to the types of diseases is possible since fluorescence believed to be derived from autoluminescence of various biochemical markers found in a urinary sample is measured and a specific point recognized in the obtained three-dimensional fluorescence spectrum is extracted. Therefore, the compatibility to various types of disease determination is increased. Furthermore, there is an advantage of achieving acceleration in the determination process since the isolation and purification processes of specific components from a urinary sample are eliminated.

In addition, sensitivity and accuracy of disease determination is further improved since the acidity of the pretreated urinary sample is adjusted to the acidity suitable for fluorescence measurement and the results of measurement of the samples for fluorescence assay in which their acidity is adjusted to various levels can be complementarily used. Furthermore, when a specific point detection map is used upon detecting a specific point, the specific point is easily and accurately specified even if the trends in the three-dimensional fluorescence spectrum are different. Additionally, a stepwise discrimination by the specific point attribute and sorting and hierarchization of the samples by grouping and categorizing allows in-depth disease determination.

SECOND EMBODIMENT

Next, disease determination method, data generation method for disease determination and data generation system for disease determination of the second embodiment will be explained.

First, the major differences from the first embodiment will be explained hereinafter In the first embodiment, the specific point attribute for the sample collected from healthy volunteers are obtained in advance and compared with the specific point attribute for the sample collected from the subject to generate disease determination data based on their sorting and hierarchized results.

In contrast, in the present embodiment, the specific point attribute or its combination of specific point attributes uniquely found in the samples from patients with various diseases such as patients with stomach cancer or colon cancer, for example, are stored as standard data for each disease type, and then disease determination data, namely sorting results or hierarchized results of the sample from the subject, are generated by comparing the known specific point attribute uniquely found in the sample from the patients with a specific disease and the combination of such attributes with the specific point attribute detected from the sample of the subject. In addition, in the present embodiment, disease determination data are obtained by taking advantage of data generation system 500 for disease determination.

(Data Generation System for Disease Determination)

First, the data generation system 500 for disease determination to suitably generate disease determination data will be explained.

The data generation system 500 for disease determination in accordance with the present embodiment is comprised of pretreatment unit 544 to perform pretreatment or adjust acidity of a urinary sample 501 in a transparent container 502 such as a quartz cell, excitation light irradiation unit 504 to irradiate the pretreated urinary sample 501 in the transparent container 502 with excitation light, emission light measurement unit 506 to measure fluorescence emitted from the urinary sample 501 in the transparent container 502 and a computer system 510 to process the results of the fluorescence measurement.

Pretreatment unit 544 is comprised of an acid and alkali supply unit 540 to supply an acid, alkali or buffer to the transparent container 502 storing the urinary sample 501 and a heating unit 542 to heat the urinary sample 501 in the transparent container 502. This pretreatment unit 544 causes chemical reactions such as hydrolysis to a part or entire biochemical component in the urinary sample by adding an acid or alkali and heating. In addition, the pretreatment unit 544 further adjusts the acidity of the urinary sample 501 of which the pretreatment is completed by adding an acid, alkali or buffer.

An excitation light irradiation unit (excitation light irradiation means) 504 irradiates the parent container 502 containing the urinary sample 501 with excitation light in a manner that its wavelength is continuously changed. At this time, it is preferable for the excitation light irradiation unit 504 to irradiate by continuously scanning a wavelength having 200-900 nm for one-photon excitation of the autoluminescent component found in the urinary sample It is further preferable to irradiate by continuously scanning the light of a wavelength having 300-600 nm. In addition, when two-photon excitation is performed to deliver less damage to the sample, it is possible to use the light with a longer wavelength, and it is preferable for the excitation light irradiation unit 504 to irradiate by continuously scanning the light of a wavelength having 400-1800 nm. It is further preferable to irradiate by continuously scanning the light of a wavelength having 600-1200 nm. In addition, when the excitation light irradiation unit 504 does not continuously scan the wavelength, the wavelength may be intermittently changed, for example.

Emission light measurement unit 506 detects fluorescence from the urinary sample 501 when the sample is irradiated with excitation light and measures its intensity. It is preferable for the emission light measurement unit 506 to measure the fluorescence wavelength in a range of 200-900 nm, more preferably 350-600 nm. This wavelength corresponds to one-photon excitation by the excitation light in the above suitable range and at the same time, the fluorescence wavelength from the autoluminescent component in the urinary sample 501 is fully covered in this manner.

A computer system 510 is a system to realize the functions of a controller 512 controlling the excitation light irradiation unit 504, the emission light measurement unit 506 and the pretreatment unit 544, a processing unit 514 to process the data from the emission light measurement unit 506, a specific point extraction unit 516 to extract the specific point from the processed data, an attribute extraction unit 518 to extract the specific point attribute, a sorting and hierarchizing unit 520 to sort and hierarchize a sample from the subject based on the extracted attribute, an output unit 522 to output the sorted and hierarchized results, a standard data generation unit 524 to generate the known specific point attribute as standard data to be used for sorting and hierarchizing and storage unit 526 to store the known specific point attributes with known hardware such as a CPU and memory and software carried out by this CPU.

The controller 512 controls the excitation light irradiation unit 504 to give instructions for the scanning condition of the wavelength of the excitation light or to give an instruction for timing of excitation light irradiation and at the same time it controls the emission light measurement unit 506 so that the emission light measurement unit 506 measures fluorescence in conjunction with the start of output by the excitation light irradiation unit 504. In addition, the controller 512 controls the pretreatment unit 514 prior to the fluorescence measurement to perform pretreatment or adjust the acidity of the urinary sample 501 as desired. All the details on the pretreatment and acidity adjustment are the same as those in the first embodiment.

The processing unit 514 obtains the wavelength scanning data of the excitation light from the excitation light irradiation unit 504, and also obtains the fluorescence wavelength and fluorescence intensity data detected in response to the excitation by the excitation light from the emission light measurement unit 506 to obtain the data of the three-dimensional fluorescence spectrum of the excitation light wavelength, fluorescence wavelength and fluorescence intensity (three-dimensional optical spectrum). In addition, the processing unit 514 performs the data correction by standardizing the fluorescence intensity of the three-dimensional fluorescence spectrum with the fluorescence intensity at some excitation light wavelength and fluorescence wavelength. With this procedure, when a plurality of samples exist and the intensities of their fluorescence have to be compared among these samples, the difference in the sample concentration in the fluorescence assay sample derived from individual physiological phenomenon can be balanced out. In addition, such correction is not limited to the method described above and, for example, a method to standardize with the concentration of the known substances found in the same urniary sample, such as creatinine can be used. In addition, in the processing unit 514, the presence or absence of the specific point can be preliminary examined with shape recognition software if needed.

The specific point extraction unit 516 extracts a specific point from the three-dimensional fluorescence spectrum processed with the processing unit 514. Here, the relative maximum peak of the fluorescence intensity is obtained as a specific point in the three-dimensional fluorescence spectrum, but the relative minimum peak of the fluorescence intensity can be obtained. In addition, a point having a 1/n of the fluorescence intensity of the relative maximum peak value (n>1) can be obtained as a specific point. The method to obtain a relative maximum peak is not to be limited, and other known methods such as the peak of fluorescence intensity is searched one by one for each range of fixed excitation light wavelength and fluorescence wavelength as a specific point, can be used. In addition, a known curve fitting method can be used.

The attribute extraction unit 518 extracts specific point attributes extracted with the specific point extraction unit 516. The specific point attribute includes wavelength coordinates of the specific point (excitation light wavelength Ex/fluorescence wavelength Em), number of specific point, intensity of fluorescence on the specific points, rate of change of the fluorescence intensity in the vicinity of the specific points and overall shape of the three-dimensional fluorescence spectrum (approximate function, changes in primary and secondary derivatives, half-value width or one-tenth value width of the relative maximum peak and peak symmetry).

The standard data generation unit (standard data generation means) 524 generates the specific point attribute in advance as a standard data to be used for the discrimination of the sample from the subject at the sorting and hierarchizing unit 520. More specifically, the standard data generation unit 524 obtains the specific point attribute of the standard samples collected from healthy bodies and the specific point attribute of the standard samples collected from the bodies having known specific diseases from the attribute extraction unit 518 to extract the known specific point attributes to discriminate the samples collected from the body of the patients having specific diseases from the samples collected from the healthy bodies by comparison.

The known specific point attribute is, for example, a specific point attribute of the sample uniquely appearing in the bodies with specific diseases or specific point attribute having a high percentage of appearance in the sample from the bodies with specific disease, and a plurality of the specific point attributes can be combined for each disease. In addition, known specific point attributes are obtained in advance for each disease type such as stomach cancer or lung cancer, for example.

The storage unit 526 stores the known specific point attributes obtained at the standard data generation unit 524 as standard data. The known specific point attributes data is, for example, stored as a data table shown in data D1 in FIG. 6, and the known specific point attributes are individually stored as $\alpha$ and $\beta$, $\gamma$ or $\delta$ corresponding to lung cancer, colon cancer and stomach cancer, respectively.

The sorting and hierarchizing unit 520 obtains the known specific point attributes correspongin to the patients with various diseases from the storage unit 526 as well as obtains the specific point attributes of the sample from the subject for disease determination from the attribute extraction unit 518. Then, the sorting and hierarchizing unit 520 compares the specific point attributes of the sample from the subject with the known specific point attributes to sort or hierarchized the sample from the subject to generate the sorting results or hierarchized results as disease determination data. More specifically, when the specific point attribute of the sample from the subject corresponds to the known specific point attribute, the sample from the subject is sorted to a group containing the known specific point attribute to generate sorting results. In contrast, when there are no matches to the known specific points, the specific point attribute of the sample from the subject will be sorted to a group of "not applicable" to generate sorting results. In addition, there are a plurality of specific point attributes, sorting is carried out in a hierarchized manner and hierarchized data are generated depending on the number of matches of the specific point attribute of the subject to the known specific point attribute.

In the present embodiment, the specific point extraction unit 516, attribute extraction unit 518 and sorting and hierarchizing unit 520 corresponds to the analyzing and sorting means.

The output unit 522 outputs such sorting results and hierarchized results to an output device such as a printer and display. The sorting data and hierarchized data which were output are the data as shown in data D2 in FIG. 6, for example, and each sample from the subject is sorted or hierarchized to either a group having $\alpha$ and $\beta$ (closely corresponding to lung cancer), a group having $\alpha$ only (relatively corresponding to lung cancer), a group having none of them (corresponding to healthy volunteer) or a group having $\gamma$ (corresponding to colon cancer).

(Disease Determination Procedure)

Next, a procedure to carry out the disease determination method and data generation method for disease determination using the data generation system 500 for disease determination will be described with reference to FIG. 7 to FIG. 10. First, prior to the disease determination of the subject, the specific point attribute or its combination uniquely found for each disease is obtained and stored as the known specific point attribute.

(Obtaining Known Specific Point)

Figure 7:
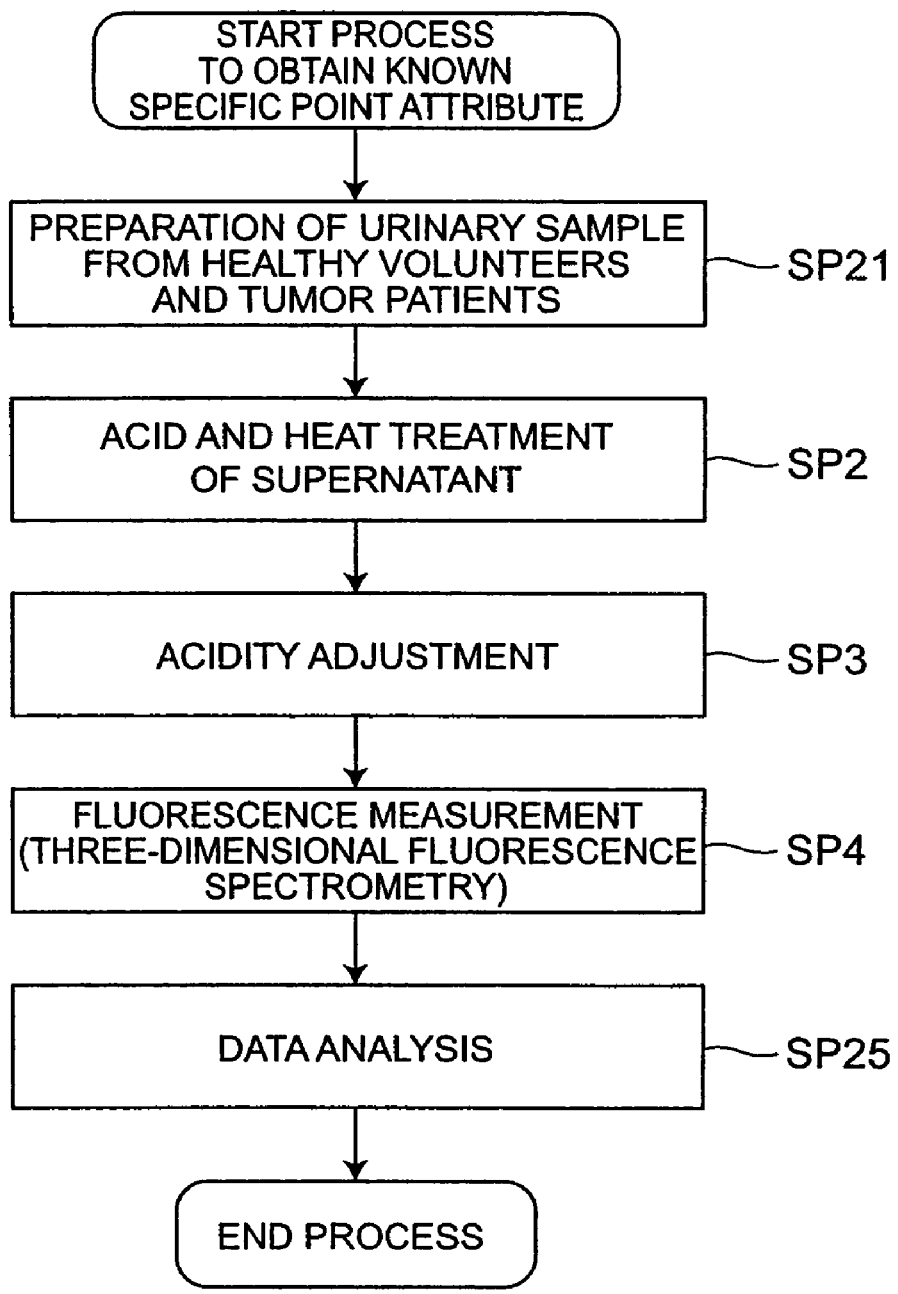
FIG. 7 shows a flowchart showing a procedure to obtain the known specific point attribute in the second embodiment.

First, as shown in FIG. 7, in step SP21, the urinary samples collected from healthy bodies and the urinary sample collected from the body with a known specific tumor are prepared and the supernatants were obtained after removing their solid components. Here, the specific tumors include stomach cancer or lung cancer, for example, and the urinary samples are prepared for each disease. Then, in steps SP2 to SP4, similar to the first embodiment, the supernatant from each urinary sample is treated with acid and heat to adjust its acidity and their fluorescence are individually measured. The acid and heat treatment or acidity adjustment are carried out by the pretreatment unit 544 and the controller 512 of the data generation system 500 for disease determination. In addition, their fluorescence is measured by the excitation light irradiation unit 504, emission light measurement unit 506 and the controller 512 of the data generation system 500 for disease determination.

Figure 8:
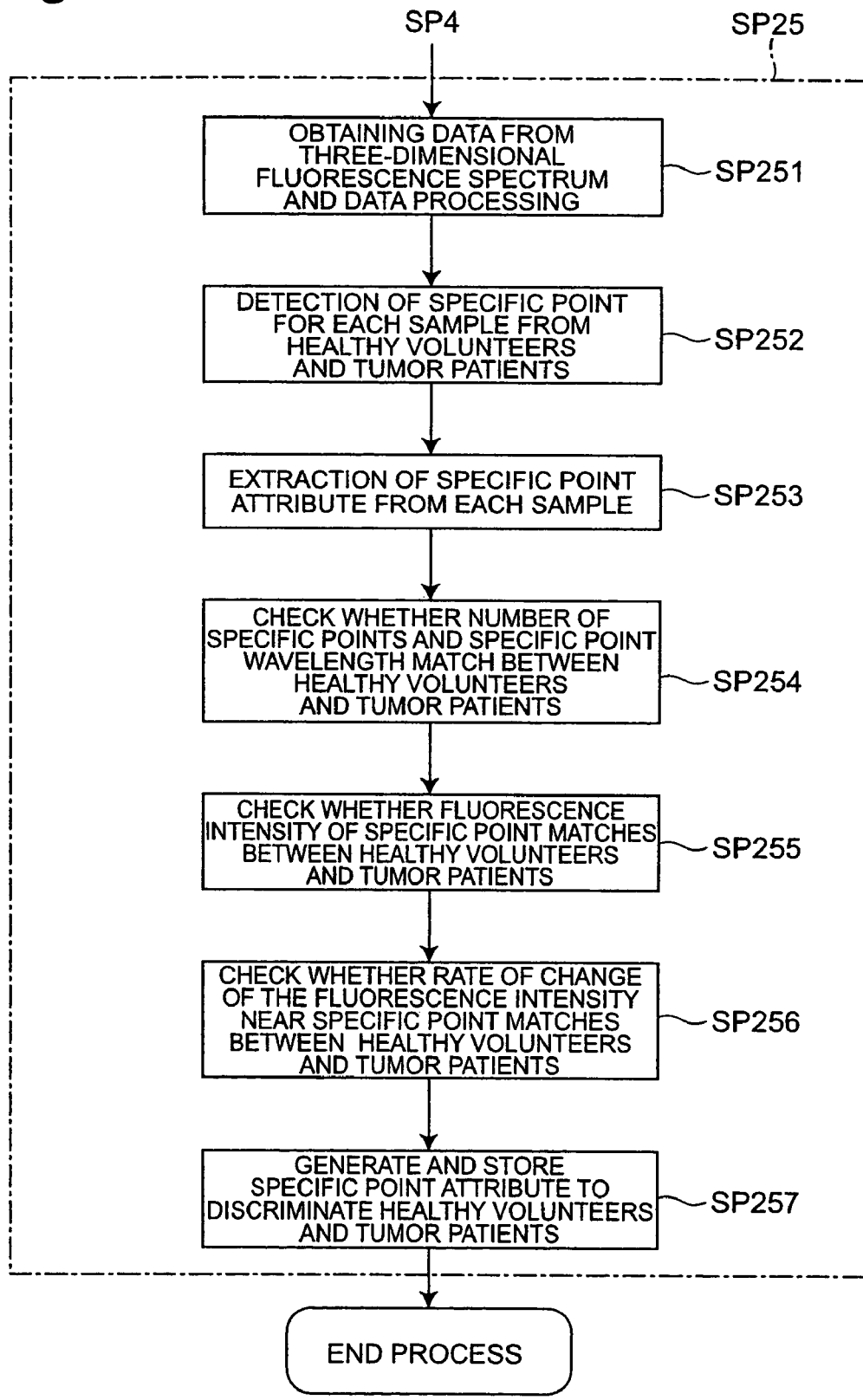
FIG. 8 is a flowchart showing a procedure (scheme) of a preferable embodiment in step SP25 of FIG. 7.

Next, it proceeds to the data analysis process in step SP25. In step SP25, as shown in FIG. 8, first in step SP251, the data of the three-dimensional fluorescence spectrum for the urinary sample from the healthy bodies and the urinary samples from the body having a tumor are individually obtained, and data correction such as standardization for each three-dimensional fluorescence spectrum is individually carried out at the processing unit 514.

Then, in step SP252, a specific point is individually detected from each three-dimensional fluorescence spectrum, in a similar manner to step SP52 in the first embodiment, at the specific point extraction unit 516.

Furthermore, in step SP253, the specific point attribute of the three-dimensional fluorescence spectrum is individually extracted at the attribute extraction unit 518.

Next, in steps SP254 to SP256, the specific point attribute of the urinary samples from healthy bodies and the specific point attribute of the urinary sample from the body with a known specific tumor are compared to generate the known specific point attributes to be used as a standard data for discriminating the body with a tumor from the healthy body in a standard data generation unit 524.

More specifically, in step SP254, by focusing attention on the number of specific points and wavelength coordinates of these specific points as the specific point attribute, it is determined whether the number of specific points and wavelength coordinates of these specific points match between the specific point attribute of the urinary samples from the healthy bodies and the specific point attribute of the urinary sample from the body having a known specific tumor.

In addition, in step SP255, by focusing attention on the fluorescence intensities of specific points of the wavelength coordinates commonly appearing in both urinary samples from the healthy bodies and from a body with a known specific tumor as the specific point attribute, it is determined whether the fluorescence intensities match between the specific point of the urinary samples from the healthy bodies and the specific point of the urinary sample from the body having a known specific tumor.

Furthermore, in step SP256, by focusing attention on the rate of change in the fluorescence intensities around the specific points commonly appearing in both urinary samples from the healthy bodies and from the body with a known specific tumor as the specific point attribute, it is determined whether the rate of change in the fluorescence intensities matches between the vicinity of the specific point of the urinary samples from the healthy bodies and the vicinity of the specific point of the urinary sample from the body having a known specific tumor.

Figure 6:
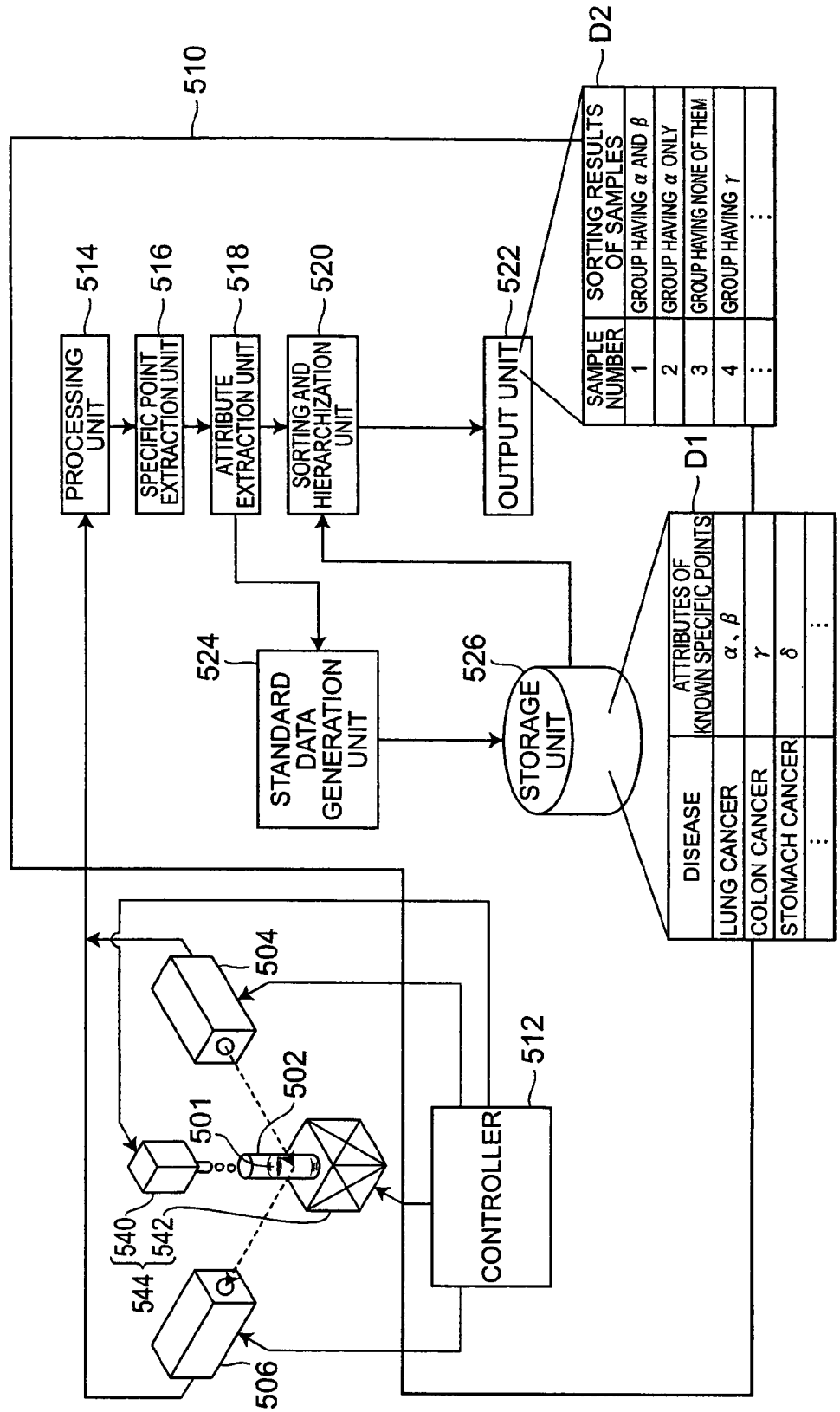
FIG. 6 shows a block diagram showing a data generation system for disease determination in accordance with the second embodiment of the present invention.

Then, in step SP257, based on the results of determination obtained from steps SP254 to SP256, the known specific point attribute of the urinary samples preferable to discriminate the patients with a tumor from healthy volunteers are obtained for each tumor type. Here, a plurality of specific point attributes may be obtained for each tumor type. Then, in step SP257, the known specific point attribute corresponds to the body having each tumor in this manner, for example, data D1 of FIG. 6 is recorded in the storage unit 526.

(Analysis of Sample from Subject)

Next, the method to determine the disease of the subject based on the known specific point attributes and the specific point attribute from the subject will be explained with reference to FIG. 9 and FIG. 10.

Figure 9:
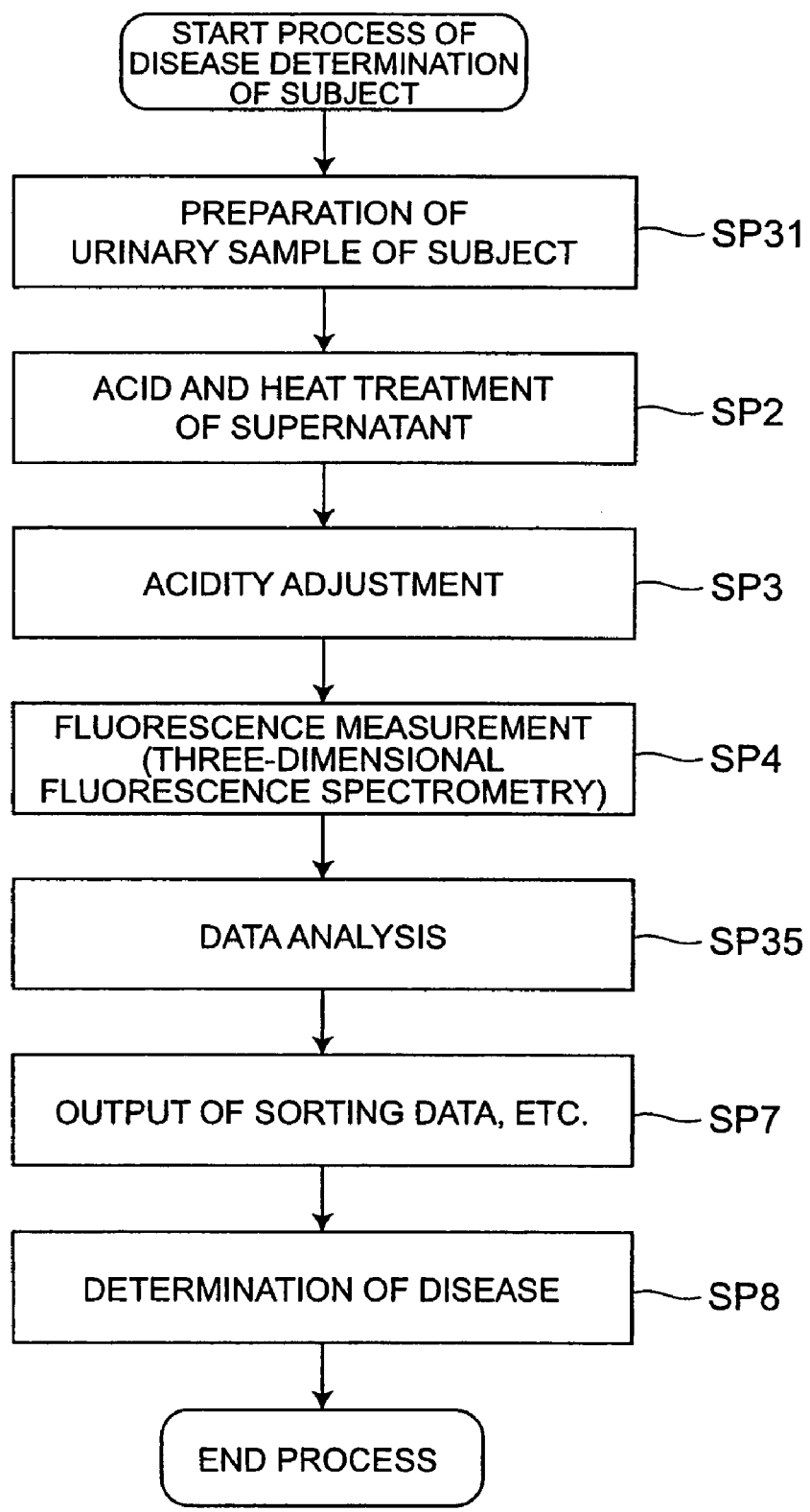
FIG. 9 is a flowchart showing a disease determination procedure in the second embodiment.

First, as shown in FIG. 9, in step SP31, the urinary sample from the subject to determine whether he/she has a disease or not is prepared to obtain the supernatant by removing the solid components. Then, in steps SP2 to SP4, similar to the flow in FIG. 7, the supernatant of the urinary sample is treated with acid and heat and its acidity is adjusted for fluorescence measure. Then, it proceeds to a data analysis process in step SP35.

Figure 10:
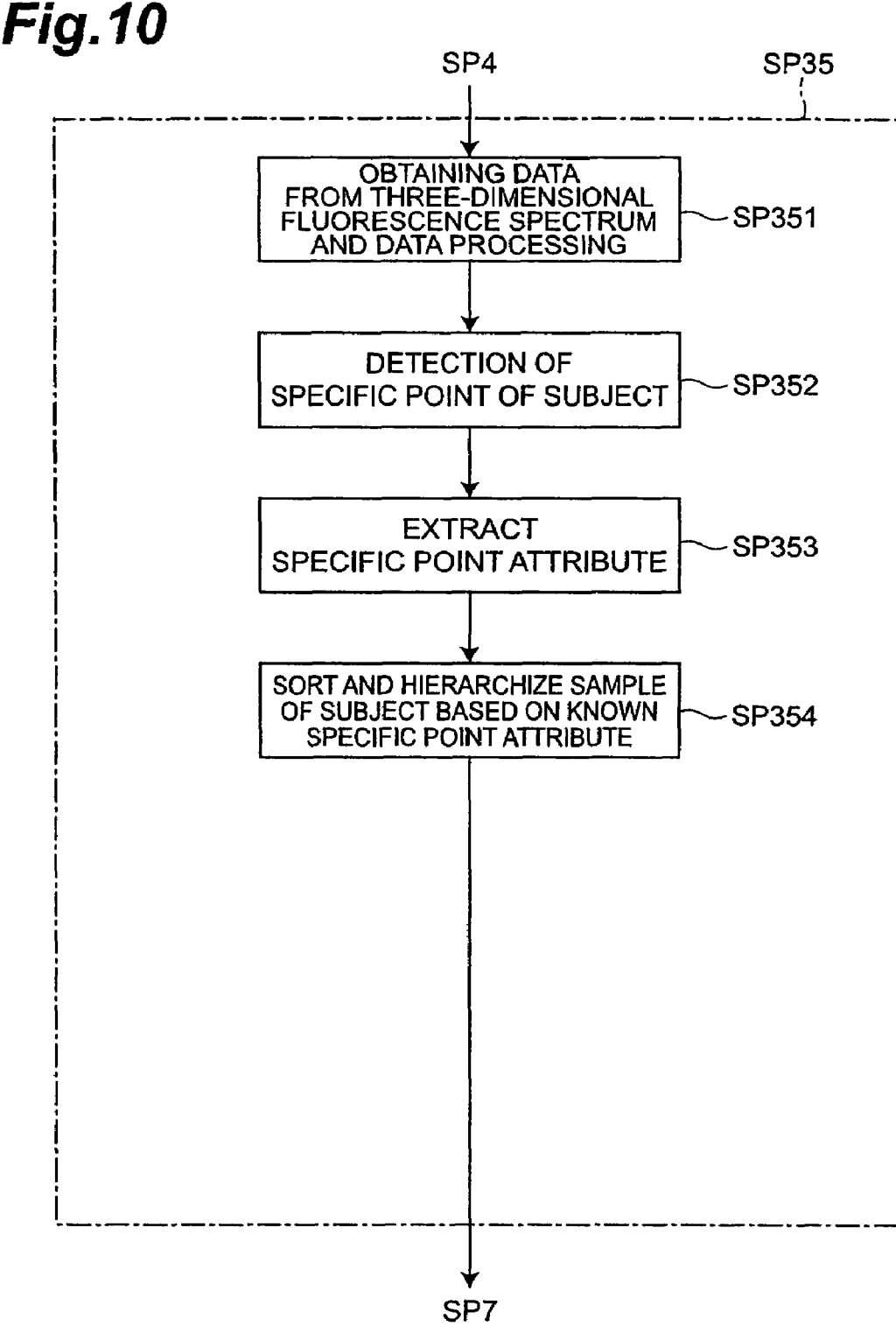
FIG. 10 is a flowchart showing a procedure (scheme) of a preferable embodiment in step SP35 of FIG. 9.

In step SP35, as shown in FIG. 10, first in step SP351, similar to Step 251 in FIG. 8, the data of the three-dimensional fluorescence spectrum for the urinary sample from the subject body are obtained and at the same time, data correction such as standardization for each three-dimensional fluorescence spectrum is carried out at the processing unit 514.

Next, in step SP352, similar to step SP252, specific point is detected from the three-dimensional optical spectrum of the urinary sample from the subject and in step SP353, similar to step SP253, the specific point attribute is extracted. Here, number of specific points, wavelength coordinates of the specific points, fluorescence intensities of the specific points and rate of change in the fluorescence intensity of the vicinity of the specific point etc. are extracted as a specific point attribute.

Then, in step SP354, the sorting and hierarchizing unit 520 compares the specific point attribute of the sample from the subject extracted at step SP518 with the known specific point attributes already stored in the storage unit 526 as the standard data, to discriminate the bodies having each type of tumor, to determine the specific point attribute of the subject matches which known specific point attribute, and to sort the sample of the subject by the matched attribute to generate sorting results. Here, when there are a plurality of known specific point attributes associated with one type of tumor, hierarchized results are generated after sorting (categorize) the urinary samples from the subject hierarchically depending on the type of the known specific point attribute matched or the number of known specific point attributes matched.

After this step, in step SP7, the output unit outputs the sorting results or hierarchized results as shown in data D2 in FIG. 6 and in step SP8, physicians etc. determine whether the subject is healthy or has a specific type of tumor or determine the likelihood of having a specific type of tumor based on such sorting results and hierarchized results.

According such an embodiment, in addition to the effects similar to the first embodiment, the sorting of the subject is promptly and accurately carried out since the specific point attribute of the subject is directly compared with the known specific point attribute of the bodies having a tumor. In addition, the known specific point attributes for discrimination are promptly obtained since the specific point attribute of the healthy bodies and the specific point attribute of the bodies with a known specific type of tumor are obtained in advance.

In addition, as shown in the case of lung cancer of data D1 of the above FIG. 6, when two known specific point attributes (α and β) are set, the disease accuracy can be evaluated since it can be hierarchized at different levels depending on whether only one factor is applied or both factors are applied.

EXAMPLES

The present invention will be further explained in detail using examples, however, the present invention is not limited to these examples.

Example 1

In the present example, it has been examined whether the discrimination of patients with malignant tumors from the healthy volunteers based on the wavelength coordinates of the specific points and the number of specific points, and one example of the known specific point attributes were obtained.

(Pretreatment of the Samples)

A total of 153 samples, including 74 samples from healthy volunteers and 79 samples from the patients with a malignant tumor, were prepared.

(Pretreatment of Urinary Samples)

All 153 samples were centrifuged at 3000 gal for 10 minutes. The supernatant of urinary samples obtained after the centrifugation was collected and then 1 ml of each supernatant was individually enclosed in a test tube with a screw cap containing 2 ml of 6 mol/L hydrochloric acid and heated at 150° C. for one hour to facilitate hydrolysis of the supernatant component.

(Acidity Adjustment of Urinary Sample)

10 μl of supernatant of the pre-treated urinary sample was individually diluted 10 times with 2 mol/L NaOH solution or 2 mol/L HCl solution to prepare an acidic sample and alkaline sample to be used for fluorescence assay.

Here, when the three-dimensional fluorescence spectrum was obtained using the two samples for fluorescence assay having those acidities in a similar manner to "fluorescence measurement" to be described later, the alkaline sample showed a significant difference between the urinary sample from the healthy volunteer and the urinary sample from a malignant tumor. Therefore, only the results obtained from the alkaline sample will be shown hereinafter. However, as described in the description of the embodiment, it is quite useful to measure the sample in an acidic solution or even in a neutral solution in addition to the sample in an alkaline solution in terms of complimenting the analysis of assay data for each other.

(Fluorescence Measurement)

Samples used for fluorescence assay are transferred to a quartz cell for fluorescence measurement after their acidities are individually adjusted and the excitation light having a wavelength at 300-600 nm was irradiated by a scanning wavelength using a fluorometer Hitachi, Ltd; Model Type: F4500). Then, the fluorescence wavelength at 350-600 nm emitted from the samples was measured to obtain the three-dimensional fluorescence spectrum. In addition, the scanning of the excitation light wavelength and fluorescence wavelength was carried out at 10 nm wavelength intervals.

(Detection of a Specific Point in the Three-dimensional Fluorescence Spectrum)

From the three-dimensional fluorescence spectrum data obtained from each sample, (1) a specific point detection map consisting of a numeric data matrix and (2) a specific point detection map consisting of contour map were prepared. For (1), the specific point on the numerical data array near the relative maximum peak (described simply as "relative maximum peak" hereinafter) of the fluorescence intensity recognized by the preliminary pattern recognition of the three-dimensional fluorescence spectrum is defined as "a wavelength coordinate when a pixel on the center of a total of 9 pixels of a 3×3 matrix (matrix components) becomes maximum" and a point satisfying this condition is specified (exacted) as its specific point.

Figure 11:
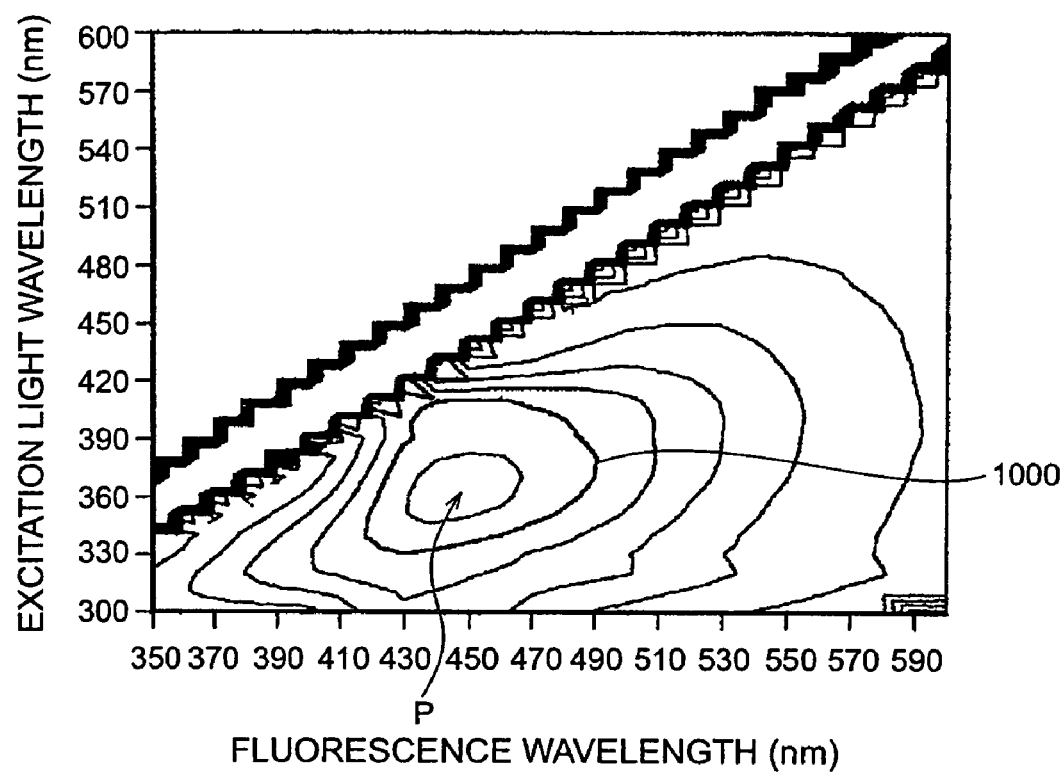
FIG. 11 shows a contour map as an example of specific point detection maps.
Figure 12:
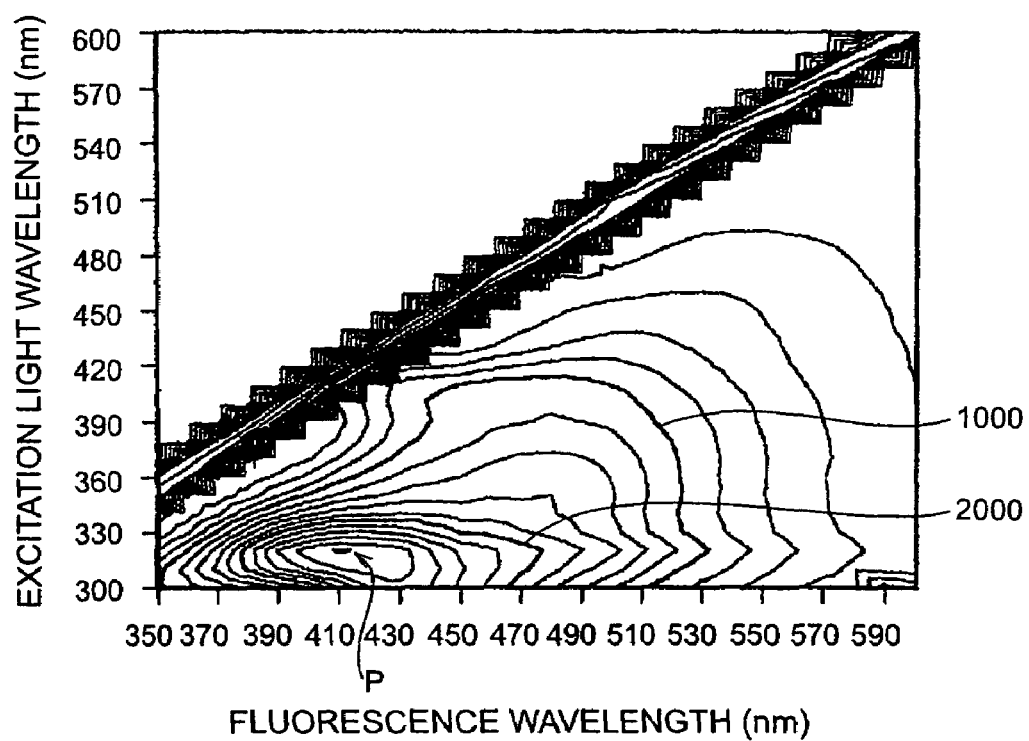
FIG. 12 shows a contour map as an example of specific point detection maps.
Figure 13:
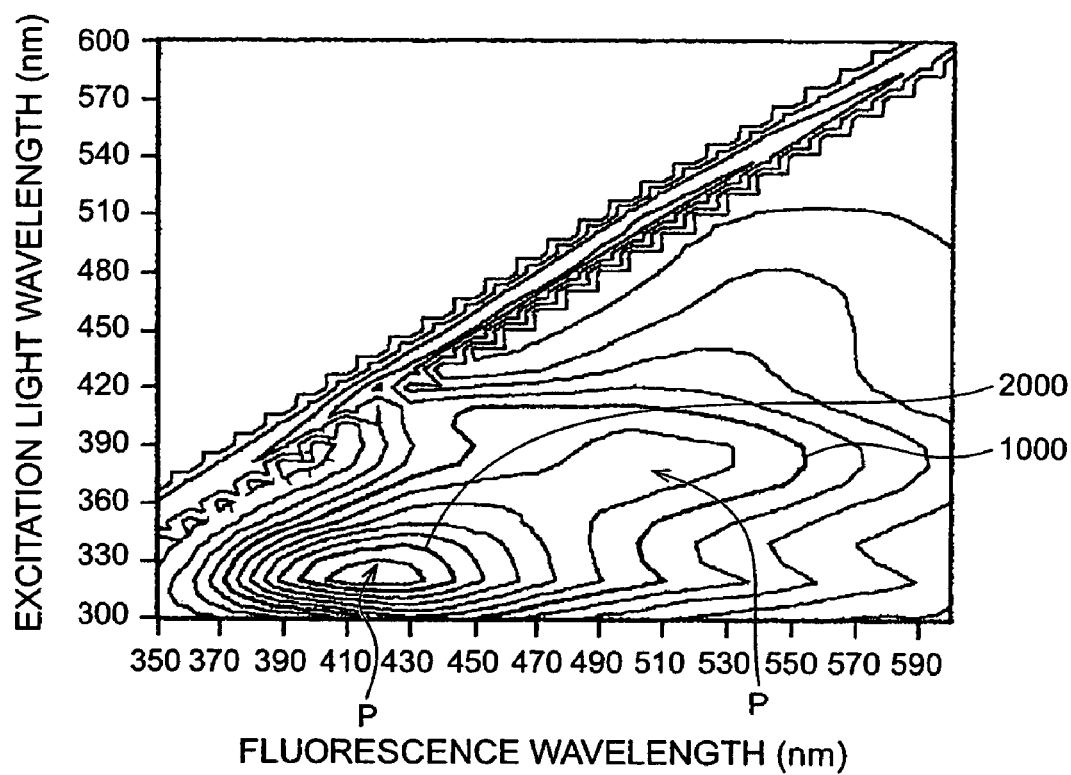
FIG. 13 shows a contour map as an example of specific point detection maps.
Figure 14:
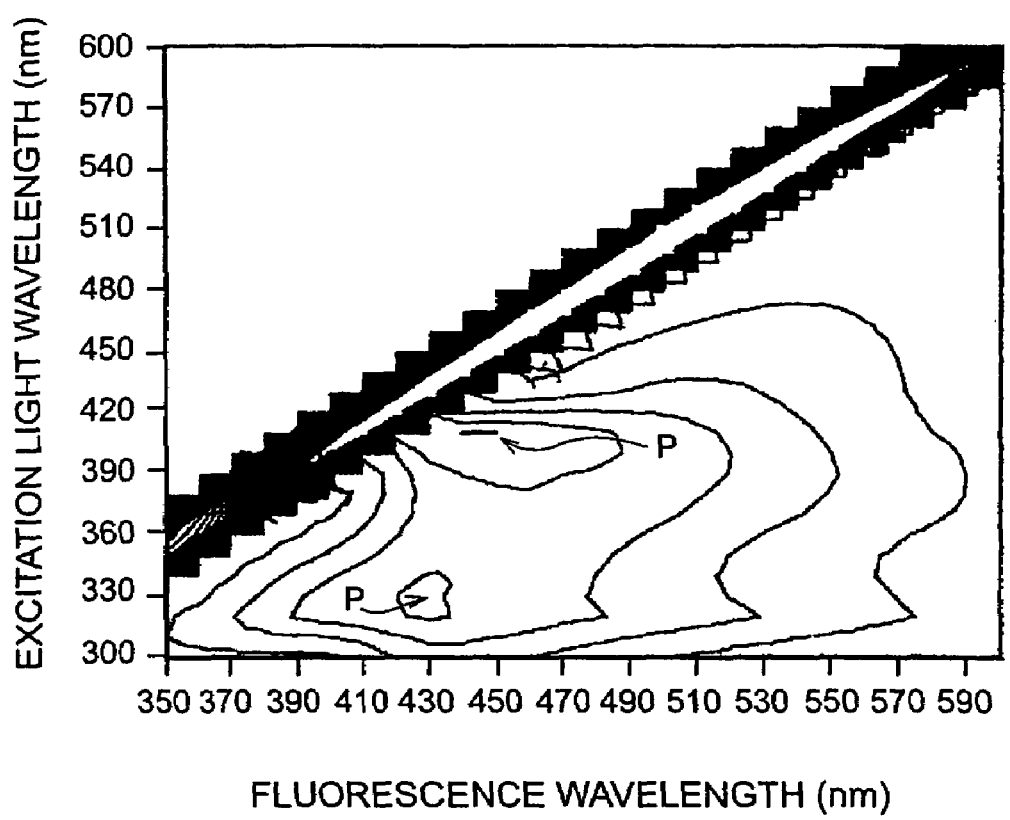
FIG. 14 shows a contour map as an example of specific point detection maps.

In addition, regarding (2), the fluorescence intensity of all wavelength coordinates are standardized so that the fluorescence intensity at Ex/Em=410 nm/450 nm becomes "1000," and a contour map was prepared using the standardized numerical data. FIG. 11 to FIG. 14 individually show an example of specific point detection maps, namely a contour map. In each figure, the interval of the contour line is 200 of fluorescence intensity after the standardization. FIG. 11 and FIG. 12 are an example of the urinary samples where one relative maximum peak P is detected as a specific point and FIG. 13 and FIG. 14 are an example where two relative maximum peaks P were detected as specific points. In addition, the contour maps shown in these FIG. 11 to FIG. 14 represent an overall shape of the three-dimensional fluorescence spectrum by themselves.

In addition, in the present example, maps standardized with the fluorescence intensity at various Ex/Em other than Ex/Em=410 nm/450 nm were also prepared. Furthermore, the concentration of creatinine in each urinary sample was quantified using a general measurement kit (for example, L Type Wako Creatinine F, Wako Pure Chemical Industries) and a map standardizing the fluorescence intensity with the concentration of creatinine was also prepared. As a result, it was confirmed that a contour map having a similar pattern, regarding the contour map shape, to ones shown in FIG. 11 to FIG. 14 of the contour map shape was obtained.

In addition, using the specific point detection map consisting of the numerical matrix of (1) described above, it was detected that the relative maximum peak exists at the same coordinate. However, there were some cases that the ability to discriminate the relative maximum peak from the background was slightly reduced when the numerical matrix of (1) described above was used. Therefore, in such a case, the combined use of two map types, the above (1) and (2) turned out to be an effective method to certainly specify the relative maximum peak P by improving an S/N ratio, namely detection sensitivity. In addition, when the map consisting of (3) vector diagram was prepared as a specific point detection map, it was confirmed that the relative maximum peak P was detected in a similar manner.

(Sorting and Hierarchization of Urinary Sample)

As described above, the attribute of the relative maximum peak detected as a specific point in the three-dimensional fluorescence spectrum, and each urinary sample was grouped (sorted). The results are summarized and shown in Table 1.

TABLE 1

|  | Number of patients with malignant tumors | Number of healthy volunteers |
|---|---|---|
| Sample group A (with P1) | 16 | 65 |
| Sample group B (without P1) | 63 | 9 |

P1 in the table shows a peak group of the wavelength coordinate below.
P1: Ex/Em = 400–410 nm/440–460 nm As shown in Table 1, it was confirmed that the patients with malignant tumors can be discriminated from the healthy volunteers with high sensitivity and specificity by focusing attention on the presence or absence of the peak group P1. More specifically, its sensitivity and specificity was 0.80 and 0.88, respectively, and this was confirmed to be similar or higher than those of the stomach cancer determination method using a pepsinogen as a marker. In short, the specific point attribute of the urinary sample collected from the subject to be determined matches with the attribute of the sample group B, and it can be determined as a malignant tumor with an accuracy at a sensitivity of 0.80 and a specificity of 0.88. More specifically, in the above embodiment, known specific point attribute is taken as "no peak group P1" and when the specific point attribute of the urinary sample from the subject satisfies this condition, the sample from this subject can be sorted to the sample group B.

In addition, the sample group was sorted according to the presence or absence of the peak group P1 and was directly determined against a malignant tumor, however, it is possible to further hierarchize by taking advantage of other attribute parameters. More specifically, it is possible to hierarchize with a parameter (new specific point attribute) of the number of maximum peaks including the peak group P1, for example. The hierarchized results obtained in this manner are shown Tables 2 and 3.

TABLE 2

| Sample group A (with P1) | | | | | |
|---|---|---|---|---|---|
| | Total peak number | | | | |
| | 0 | 1 | 2 | 3 | 4 |
| Number of patients with malignant tumors | 0 | 4 | 7 | 3 | 2 |
| Number of healthy volunteers | 0 | 11 | 44 | 6 | 4 |

TABLE 3

| Sample group B (without P1) | | | | | |
|---|---|---|---|---|---|
| | Total peak number | | | | |
| | 0 | 1 | 2 | 3 | 4 |
| Number of patients with malignant tumors | 4 | 37 | 16 | 6 | 0 |
| Number of healthy volunteers | 0 | 8 | 1 | 0 | 0 |

Tables 2 and 3 shows hierarchized results of the sample groups A and B shown in Table 1 based on the total number of peaks. These tables indicate that hierarchization is quite difficult for the sample group A, whereas the hierarchization is possible for the sample group B when the total number of peaks is added as a new parameter. More specifically, among the samples belonging to the sample group B, the sample having the total peak number of 0 and 3 consist of samples from tumor patients only (See Table 3), indicating that the hierarchization of the sample group B is possible. When the hierarchizaton by such a total peak number as one of the parameters are performed on the sample group B, the results shown in Table 4 were obtained.

TABLE 4

| | Number of patients with malignant tumors | Number of healthy volunteers |
|---|---|---|
| Sample group A (with P1) | 16 | 65 |
| Sample group B-1 (without P1-total peak number 1 or 2) | 53 | 9 |
| Sample group B-2 (without P1-total peak number 0 or 3) | 10 | 0 |

When the determination of a malignant tumor is carried out based on Table 4, the addition of the total peak number as a parameter resulted in the determination of a malignant tumor with higher accuracy although there is no major difference in the determination results (sensitivity and specificity) from the results shown in Table 1. In short, Table 4 shows that the sample group B determined to be the patients with a malignant tumor can be hierarchized to the sample group B-2 of the malignant tumor patients with higher accuracy and the sample group B-1 of the malignant tumor patients with less accuracy. Therefore, when the determination of a malignant tumor is carried out based on Table 4, the determination of a malignant tumor is possible with higher accuracy by sorting the samples in a hierarchized fashion according to the total number of peaks as a new known specific point attribute although there is no major difference in the determination results (sensitivity and specificity) from the results shown in Table 1. In short, when the specific point attribute of the urinary sample from the subject is sorted and hierarchized to be a match with the attribute of the sample group B-2 based on Table 4, it can be determined that this subject is very likely to have a malignant tumor. More specifically, the known specific point attribute in the above embodiment is taken as the "no peak group P1" and the "total peak number is 0 or 3," for example, the sample of the subject is sorted to be in the sample group B-2 when the specific point attribute of the urinary sample from the subject satisfies both conditions.

Example 2

In the present example, it has been examined whether the discrimination of patients with malignant tumors from the healthy volunteers based on the rate of changes in the emission light (fluorescence) intensity of the periphery of the specific point, and one example of the known specific point attributes were obtained. First, similar to Example 1, the processes from (sample preparation) to (specific point detection in the three-dimensional fluorescence spectrum) were carried out.

(Sorting and Hierarchization of Urinary Sample)

The representative coordinate of the peak group P1 shown in Example 1 is as Ex/Em=410 nm/450 nm, and when attention was focused on the ratio of the fluorescence intensity at the coordinate and the fluorescence intensity of the periphery of the coordinate, especially the ratio of the fluorescence intensity at Ex/Em=410 nm/450 nm and the fluorescence intensity at the Ex/Em=400 nm/480 nm turned out to be significantly different between the healthy volunteers and the patients with malignant tumors. In the table, Ia shows the fluorescence intensity at Ex/Em=400 nm/480 nm, and Ib shows the fluorescence intensity at Ex/Em=410 nm/450 nm. The results are shown in Table 5.

TABLE 5

| | Number of patients with malignant tumors | Number of healthy volunteers |
|---|---|---|
| Sample group C (Ia/Ib: Less than 1.1) | 16 | 63 |
| Sample group D (Ia/Ib: Equal or more than 1.1) | 63 | 11 |

As shown in Table 5, it was confirmed that the patients with malignant tumors can be discriminated from the healthy volunteers with high sensitivity and specificity similar to the case of Example 1 by focusing attention on the rate of changes in the fluorescence intensity of the periphery of the peak group P1. More specifically, its sensitivity and specificity was 0.80 and 0.85, respectively. In short, the specific point attribute of the urinary sample collected from the subject to be determined matches with the attribute of the sample group D, and it can be determined as a malignant tumor with an accuracy at a sensitivity of 0.80 and a specificity of 0.85. Therefore, in the above embodiment, the known specific point attribute is taken as "Ia/Ib is equal to or larger than 1.1" and when the specific point attribute of the urinary sample from the subject satisfies this condition, the sample from this subject can be sorted to the sample group D.

Example 3

In the present example, it has been examined whether the discrimination of the patients with malignant tumors from the healthy volunteers based on the emission light (fluorescence) intensity of a specific point, and one example of the known specific point attributes were obtained. First, similar to Example 1, the processes from (sample preparation) to (specific point detection in the three-dimensional fluorescence spectrum) were carried out.

(Sorting and Hierarchization of Urinary Sample)

Similar to the case of Example 2, the representative coordinate of the peak group P1 shown in Example 1 is determined as Ex/Em=410 nm/450 nm and when attention was focused on the fluorescence intensity at the coordinate, it was confirmed that the values that standardized fluorescence intensity with the creatinine concentration are different between the healthy volunteers and the patients with malignant tumors. The results are shown in Table 6.

TABLE 6

| | Number of patients with malignant tumors | Number of healthy volunteers |
|---|---|---|
| Sample group E (Ib/CRE: Equal or more than 0.947) | 21 | 63 |
| Sample group F (Ib/CRE: Less than 0.947) | 58 | 11 |

In the table, Ib indicates the fluorescence intensity at the coordinate of Ex/Em=410 nm/450 nm and CRE indicates the creatinine concentration (mg/dl). As shown in Table 6, it was confirmed that the patients with malignant tumors can be discriminated from the healthy volunteers with high sensitivity and specificity by focusing attention on the values that standardized fluorescence intensity at the coordinate of Ex/Em=410 nm/450 nm with the creatinine concentration.

More specifically, its sensitivity and specificity was 0.73 and 0.85, respectively. In short, the specific point attribute of the urinary sample collected from the subject to be determined matches with the attribute of the sample group F, and it can be determined as a malignant tumor with accuracy at a sensitivity of 0.73 and a specificity of 0.85. More specifically, in the above embodiment, the known specific point attribute is taken as "Ib/CRE is less than 0.947" when the specific point attribute of the urinary sample from the subject satisfies this condition, the sample can be sorted to the sample group F.

In addition, regarding the fluorescence intensity standardized with the creatinine concentration, it was confirmed that not only the fluorescence intensity at the coordinate of Ex/Em=410 nm/450 nm but the sum of the fluorescence intensities of the peak groups P1 was standardized with the creatinine concentration are significantly different between the healthy volunteers and the patients with malignant tumors. The results are shown in Table 7. In addition, the sum of the values of the standardized fluorescence intensity at the above peak group P1 with the creatinine concentration was the sum of the values standardized the respective fluorescence intensities at the coordinates of Ex/Em=400 nm/440 nm, 400 nm/450 nm, 400 nm/460 nm, 410 nm/440 nm, 410 nm/450 nm and 410 nm/460 nm with the creatinine concentration.

TABLE 7

|  | Number of patients with malignant tumors | Number of healthy volunteers |
| --- | --- | --- |
| Sample group G [Sum of (fluorescence intensity/CRE): Equal or more than 5.858] | 20 | 62 |
| Sample group H [Sum of (fluorescence intensity/CRE): Less than 5.858] | 59 | 12 |

In the table, the sum of (fluorescence intensity/CRE) indicates the sum of the values standardized the respective fluorescence intensity of the coordinates at Ex/Em=400 nm/440 nm, 400 nm/450 nm, 400 nm/460 nm, 410 nm/440 nm, 410 nm/450 nm and 410 nm/460 nm with the creatinine concentration (mg/dl). As shown in Table 7, it was confirmed that the patients with malignant tumors can be ddiscriminated from the healthy volunteers with high sensitivity and specificity by focusing attention on the sum of the values that standardized fluorescence intensity of the peak group P1 with the creatinine concentration. More specifically, its sensitivity and specificity was 0.75 and 0.84, respectively. In short, the specific point attribute of the urinary sample collected from the subject to be determined matches with the attribute of the sample group H, and it can be determined as a malignant tumor with accuracy at a sensitivity of 0.75 and a specificity of 0.84. More specifically, in the above embodiment, the known specific point attribute is taken as "the sum of (fluorescence intensity/CRE) is less than 5.858" and when the specific point attribute of the urinary sample from the subject satisfies this condition, the sample from this subject can be sorted to the sample group H.

Example 4

In the present example, it has been examined whether the discrimination of the patients with malignant tumors from the healthy volunteers from different perspectives from Example 1 according to the wavelength coordinates of the specific points, other examples of known specific point attributes were obtained. First, similar to Example 1, the processes from (sample preparation) to (specific point detection in the three-dimensional fluorescence spectrum) were carried out.

(Sorting and Hierarchization of Urinary Sample)

When the attention was focused on the peak coordinates other than the peak group P1 used in Examples 1 to 3 and the peak group P2 commonly detected in the samples from the patients with malignant tumors and healthy volunteers, it was confirmed that there is a peak group where the occurrence is quite different between the healthy volunteers and the patients with malignant tumors. In addition, the peak group P2 indicates the peak group of wavelength coordinates at Ex/Em=310 nm/430 nm, 320 nm/410 nm, 320 nm/420 nm, 320 nm/430 nm and 330 nm/410 nm.

Figure 15:
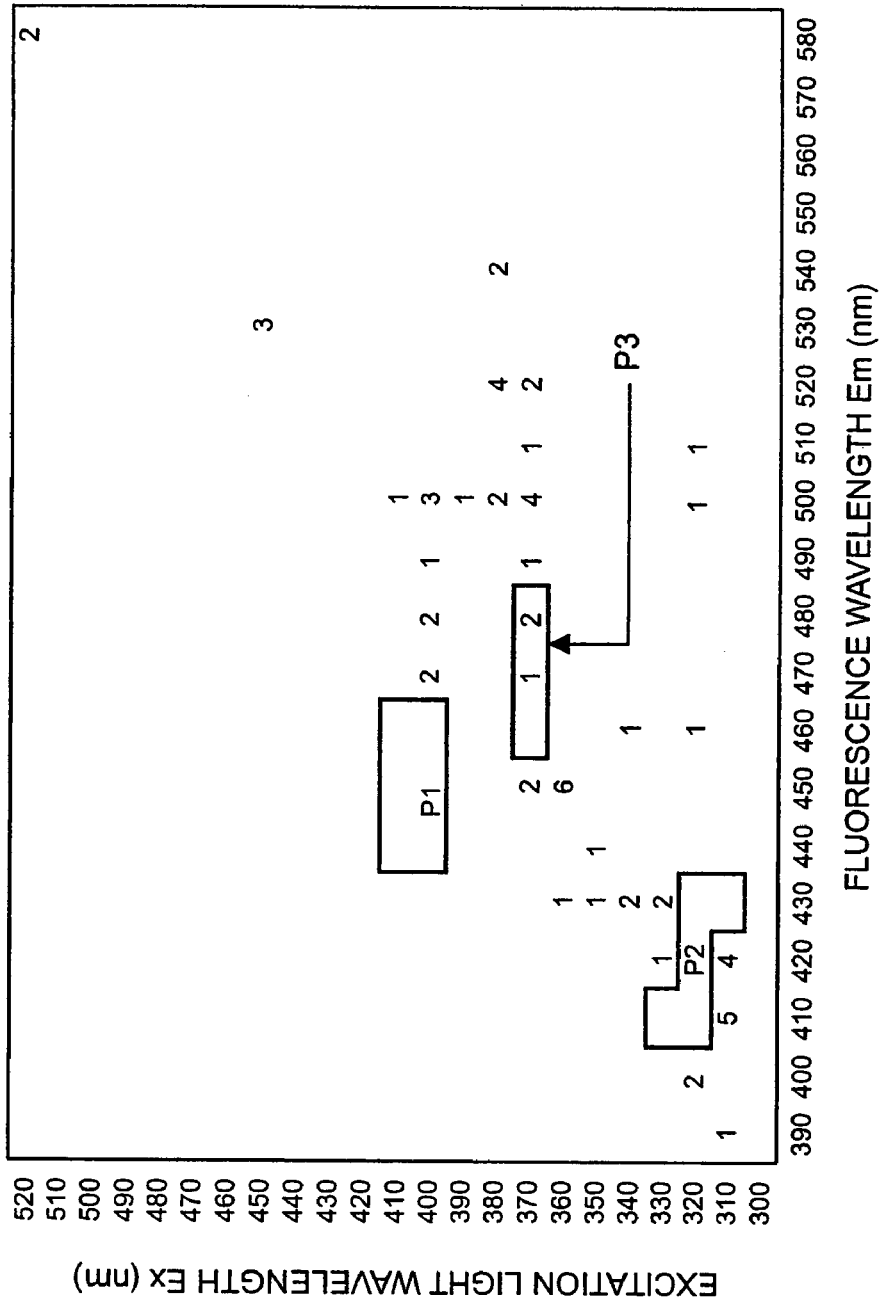
FIG. 15 is a figure showing the number of samples for which peak is detected at the corresponding coordinates from the patients with a malignant tumor in the example 4.
Figure 16:
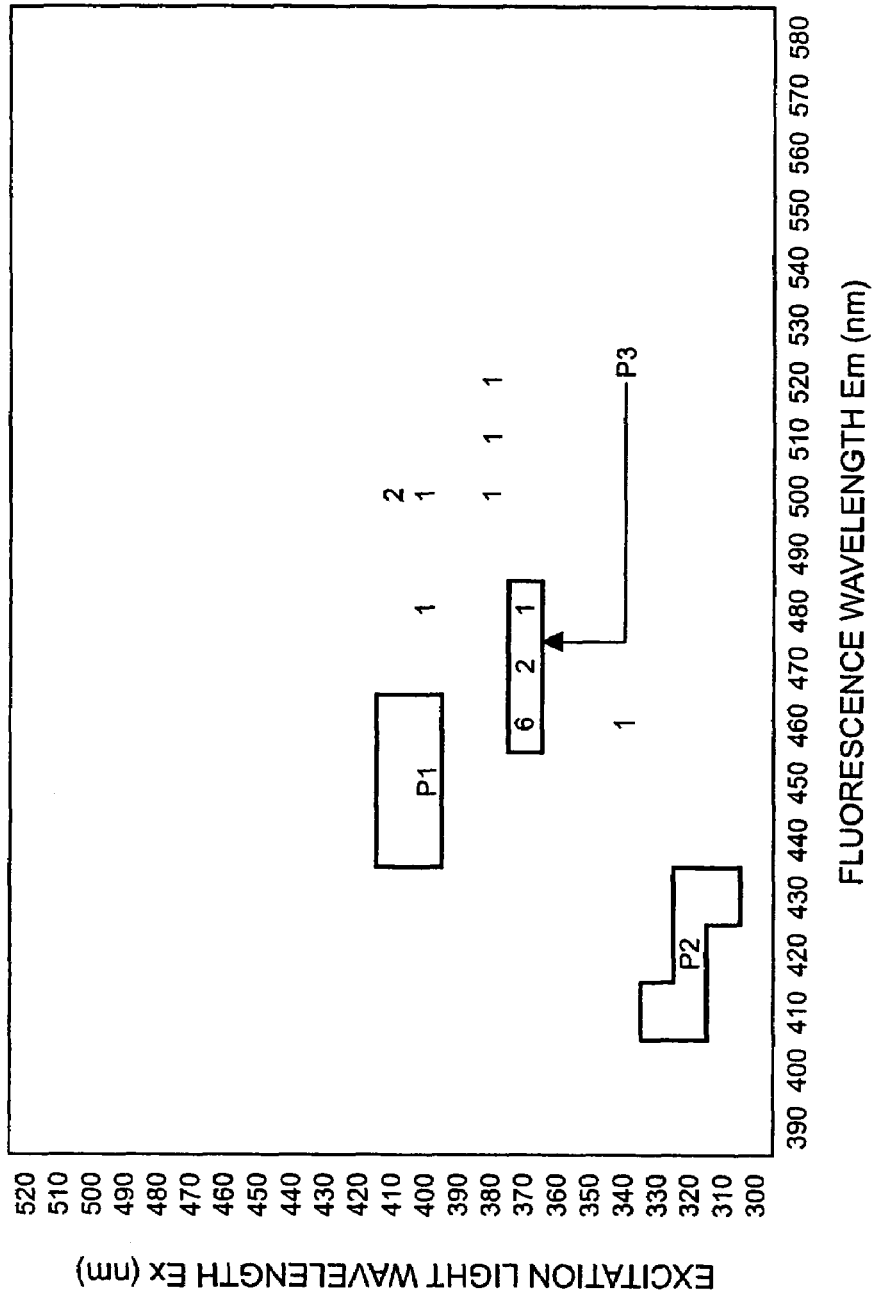
FIG. 16 is a figure showing the number of samples for which peak is detected at the corresponding coordinates from the healthy volunteers in the example 4.

FIG. 15 shows a figure illustrating the number of samples for which the peak was detected at each coordinate in the patients with malignant tumors, and FIG. 16 shows a figure illustrating the number of samples for which the peak was detected at each coordinate in the healthy volunteers. Both FIG. 15 and FIG. 16 do not show the number of samples detected in the peak groups P1 and P2, but show their coordinate areas only. In addition, an area of peak group P3 to be described later is also shown in FIG. 15 and FIG. 16.

When FIG. 15 and FIG. 16 are compared, more peaks are detected in the samples from the patients with malignant tumors in terms of the area excluding the peak groups P1, P2 and P3, and the coordinates for which the peaks are detected range across a broad area. Here, the peak group P3 is the area covering three coordinates in Ex/Em=370 nm/460-480 nm and also the area for which the peak tends to appear at a high ratio in both healthy volunteers and the patients with malignant tumors, or the area for which the peak tends to appear more easily in the healthy volunteers.

Then, Table 8 shows that more peaks are found in the patients with malignant tumors in comparison with the healthy volunteers in the coordinates other than the peak groups P1, P2 and P3 peak group P4, hereinafter). In addition, the total number of the samples shown in FIG. 15 and FIG. 16 does not match with the number of samples detected at the peak group P4 since a plurality of peaks may be detected in some samples.

TABLE 8

|  | Number of patients with malignant tumors | Number of healthy volunteers |
| --- | --- | --- |
| Sample group I (With peak at P4) | 50 | 7 |
| Sample group J (Without peak at P4) | 29 | 67 |

As shown in Table 8, it was confirmed that the patients with malignant tumors can be discriminated from the healthy volunteers with high sensitivity and specificity although such sensitivity and specificity are slightly less than those of Examples 1 to 3, by focusing attention on the presence or absence of the peak at the peak group P4 other than peak groups P1, P2 and P3. More specifically, its sensitivity and specificity was 0.63 and 0.91, respectively. In short, the specific point attribute of the urinary sample collected from the subject to be determined matches with the attribute of the sample group I, and it can be determined as a malignant tumor with accuracy at a sensitivity of 0.63 and a specificity of 0.91. More specifically, in the above embodiment, the known specific point attribute is taken as "with peak at peak group P4" and when the specific point attribute of the urinary sample from the subject satisfies this condition, the sample from this subject can be sorted to the sample group I.

As described above, the discrimination of the healthy volunteers and the patients with malignant tumors was individually described by using two attribute parameters in Example 1 and using a single parameter in Examples 2 to 4, the procedure to prepare the known specific point attributes were also shown, and furthermore systematic hierarchical sorting of the samples can be achieved by using various different parameters obtained from the three-dimensional fluorescence spectrum for the discrimination of specific points in an appropriate order.

INDUSTRIAL APPLICABILITY

In accordance with the disease determination method, data generation method for disease determination and data generation system for disease determination of the present invention, the invention sufficiently improves the determination veracity and accuracy upon determining specific diseases such as malignant tumors using a sample from the body and has a potential for various applications of disease determination as well as achieves acceleration in the determination process.

The invention claimed is:

1. Data generation method for disease determination for generating data for disease determination using a biological sample obtained from the subject, comprising;
    pretreatment process to add an acidic or alkaline solution to the sample and to heat the sample,
    excitation light irradiation process to irradiate the sample with the excitation light and to continuously or intermittently change the wavelength of the excitation light,
    emission light measurement process to measure the wavelength and intensity of the emission light emitted from the sample in response to the excitation light, and
    analyzing and sorting process to detect a specific point in the three-dimensional optical spectrum composed of the excitation light wavelength, emission light wavelength and emission light intensity and to sort the sample based on an attribute of the specific point, wherein the specific point is a relative maximum peak or a relative minimum peak of a fluorescence intensity and is utilized for disease determination.

2. The data generation method for disease determination according to claim 1, wherein a specific point attribute is determined by at least one of the parameters selected from the group consisting of wavelength coordinates of said specific point, number of the specific points, intensity of said emission light of the specific point, rate of change in the emission light intensity on the periphery of the specific point and said three-dimensional optical spectrum shape in said analyzing and sorting process.

3. The data generation method for disease determination according to claim 1, wherein urine is used as said sample.

4. The data generation method for disease determination according to claim 1, wherein fluorescence is measured as said emission light.

5. The data generation method for disease determination according to claim 1, wherein
    the light having a wavelength in a range of 200-900 nm as said excitation light in said excitation light irradiation process and
    fluorescence having a wavelength in a range of 200-900 nm as said emission light in said emission light measurement process.

6. The data generation method for disease determination according to claim 1, wherein the acidity adjustment process to adjust acidity of said sample is further included after said pretreatment process is performed.

7. The data generation method for disease determination according to claim 6, wherein acidity of said sample is arbitrarily selected from acidic, alkaline, neutral or almost neutral and an acid, alkali or buffer is added to the sample to achieve the acidity selected during said acidity adjustment process.

8. The data generation method for disease determination according to claim 7, wherein the acidity of said sample is maintained in alkaline during said acidity adjustment process.

9. The data generation method for disease determination according to claim 1, wherein said specific point is at least one of a relative maximum peak, a relative minimum peak and a point having 1/n of the intensity of the relative maximum peak (n>1) of said emission light in said three-dimensional optical spectrum in said analyzing and sorting process.

10. The data generation method for disease determination according to claim 9, wherein specific point detection maps selected from the group consisting of a numerical matrix, contour map and vector diagram on said three-dimensional coordinate system are prepared and said specific point is detected based on the specific point detection map in said analyzing and sorting process.

11. The data generation method for disease determination according to claim 1, wherein the specific point attribute of said sample subject for the examination and the known specific point attributes detected in advance using the standard samples from the bodies having a known specific type of disease are compared and the sample is sorted according to the comparison results in said analyzing and sorting process.

12. The data generation method for disease determination according to claim 11, wherein the standard data generation process is included to generate said known specific point attributes based on the comparison results of the specific point attribute detected using the standard samples from the healthy bodies with the specific point attribute detected using the standard samples from the bodies having a known specific type of disease.

13. The data generation method for disease determination according to claim 1, wherein said disease is a malignant tumor.

* * * * *